(12) United States Patent
Bullington et al.

(10) Patent No.: US 11,317,838 B2
(45) Date of Patent: *May 3, 2022

(54) SYRINGE-BASED FLUID DIVERSION MECHANISM FOR BODILY FLUID SAMPLING

(71) Applicant: Magnolia Medical Technologies, Inc., Seattle, WA (US)

(72) Inventors: Gregory J. Bullington, Seattle, WA (US); Richard G. Patton, Seattle, WA (US); Shan E. Gaw, Seattle, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/388,979

(22) Filed: Jul. 29, 2021

(65) Prior Publication Data

US 2021/0353194 A1 Nov. 18, 2021

Related U.S. Application Data

(63) Continuation of application No. 16/255,058, filed on Jan. 23, 2019, now abandoned, which is a
(Continued)

(51) Int. Cl.
*A61B 5/15* (2006.01)
*A61B 5/153* (2006.01)
(Continued)

(52) U.S. Cl.
CPC ...... *A61B 5/150251* (2013.01); *A61B 5/1405* (2013.01); *A61B 5/1416* (2013.01);
(Continued)

(58) Field of Classification Search
CPC ............ A61B 5/150251; A61B 5/1405; A61B 5/1416; A61B 5/1427; A61B 5/1438;
(Continued)

(56) References Cited

U.S. PATENT DOCUMENTS 2,707,953 A 5/1955 Ryan
2,992,974 A 7/1961 Belcove et al.
(Continued)

FOREIGN PATENT DOCUMENTS

CN 2115767 U 9/1992
CN 2907683 Y 6/2007
(Continued)

OTHER PUBLICATIONS

Office Action for U.S. Appl. No. 11/955,635, dated Jul. 22, 2010, 11 pages.
(Continued)

*Primary Examiner* — Sean P Dougherty
*Assistant Examiner* — Alexander H Connor
(74) *Attorney, Agent, or Firm* — Cooley LLP

(57) ABSTRACT

A syringe-based device includes a housing, a pre-sample reservoir, and an actuator. The housing defines an inner volume between a substantially open proximal end portion and a distal end portion that includes a port couplable to a lumen-defining device. The pre-sample reservoir is fluidically couplable to the port to receive and isolate a first volume of bodily fluid. The actuator is at least partially disposed in the inner volume and has a proximal end portion that includes an engagement portion and a distal end portion that includes a sealing member. The engagement portion is configured to allow a user to selectively move the actuator between a first configuration such that bodily fluid can flow from the port to the pre-sample reservoir, and a second configuration such that bodily fluid can flow from the port to a sample reservoir defined at least in part by the sealing member and the housing.

54 Claims, 16 Drawing Sheets

Related U.S. Application Data continuation of application No. 14/880,397, filed on Oct. 12, 2015, now Pat. No. 10,206,613, which is a continuation of application No. 14/094,073, filed on Dec. 2, 2013, now Pat. No. 9,155,495.

(60) Provisional application No. 61/731,620, filed on Nov. 30, 2012.

(51) Int. Cl.
 *A61B 10/00* (2006.01)
 *A61B 5/154* (2006.01)
 *A61B 5/155* (2006.01)
 *B01L 3/02* (2006.01)

(52) U.S. Cl.
 CPC .......... *A61B 5/1427* (2013.01); *A61B 5/1438* (2013.01); *A61B 5/15003* (2013.01); *A61B 5/153* (2013.01); *A61B 5/154* (2013.01); *A61B 5/155* (2013.01); *A61B 5/150221* (2013.01); *A61B 5/150236* (2013.01); *A61B 5/150244* (2013.01); *A61B 5/150343* (2013.01); *A61B 5/150389* (2013.01); *A61B 5/150633* (2013.01); *A61B 10/0045* (2013.01); *A61B 5/150732* (2013.01); *B01L 3/0231* (2013.01)

(58) Field of Classification Search
 CPC .......... A61B 5/15003; A61B 5/150221; A61B 5/150236; A61B 5/150244; A61B 5/150343; A61B 5/150389; A61B 5/150633; A61B 5/153; A61B 5/154; A61B 5/155; A61B 5/150732; A61B 10/0045; B01L 3/0231
 See application file for complete search history.

(56) References Cited

U.S. PATENT DOCUMENTS

| | | |
|---|---|---|
| 3,013,557 A | 12/1961 | Pallotta |
| 3,098,016 A | 7/1963 | Cooper et al. |
| 3,382,865 A | 5/1968 | Worral, Jr. |
| 3,405,706 A | 10/1968 | Cinqualbre |
| 3,467,095 A | 9/1969 | Ross |
| 3,494,351 A | 2/1970 | Horn |
| 3,494,352 A | 2/1970 | Russo et al. |
| 3,577,980 A | 5/1971 | Cohen |
| 3,604,410 A | 9/1971 | Whitacre |
| 3,635,798 A | 1/1972 | Kirkham et al. |
| 3,648,684 A | 3/1972 | Barnwell et al. |
| 3,680,558 A | 8/1972 | Kapelowitz |
| 3,730,168 A | 5/1973 | Mcwhorter |
| 3,741,197 A | 6/1973 | Sanz et al. |
| 3,777,773 A | 12/1973 | Tolbert |
| 3,803,810 A | 4/1974 | Rosenberg |
| 3,817,240 A | 6/1974 | Ayres |
| 3,831,602 A | 8/1974 | Broadwin |
| 3,834,372 A | 9/1974 | Turney |
| 3,835,835 A | 9/1974 | Thompson et al. |
| 3,848,579 A | 11/1974 | Villa-Real |
| 3,848,581 A | 11/1974 | Cinqualbre et al. |
| 3,874,367 A | 4/1975 | Ayres |
| 3,886,930 A | 6/1975 | Ryan |
| 3,890,203 A | 6/1975 | Mehl |
| 3,890,968 A | 6/1975 | Pierce et al. |
| 3,937,211 A | 2/1976 | Merten |
| 3,945,380 A | 5/1976 | Dabney et al. |
| 3,960,139 A | 6/1976 | Bailey |
| 3,978,846 A | 9/1976 | Bailey |
| 4,056,101 A | 11/1977 | Geissler et al. |
| 4,057,050 A | 11/1977 | Sarstedt |
| 4,063,460 A | 12/1977 | Svensson |
| 4,077,395 A | 3/1978 | Woolner |
| 4,106,497 A | 8/1978 | Percarpio |
| 4,133,304 A | 1/1979 | Bailey |
| 4,133,863 A | 1/1979 | Koenig |
| 4,150,089 A | 4/1979 | Linet |
| 4,154,229 A | 5/1979 | Nugent |
| 4,166,450 A | 9/1979 | Abramson |
| 4,190,426 A | 2/1980 | Ruschke |
| 4,193,400 A | 3/1980 | Loveless et al. |
| 4,207,870 A | 6/1980 | Eldridge |
| 4,210,173 A | 7/1980 | Choksi et al. |
| 4,212,308 A | 7/1980 | Percarpio |
| 4,238,207 A | 12/1980 | Ruschke |
| 4,257,416 A | 3/1981 | Prager |
| 4,275,730 A | 6/1981 | Hussein |
| 4,298,358 A | 11/1981 | Ruschke |
| 4,340,067 A | 7/1982 | Rattenborg |
| 4,340,068 A | 7/1982 | Kaufman |
| 4,349,035 A | 9/1982 | Thomas et al. |
| 4,370,987 A | 2/1983 | Bazell et al. |
| 4,398,544 A | 8/1983 | Nugent et al. |
| 4,411,275 A | 10/1983 | Raitto |
| 4,412,548 A | 11/1983 | Hoch |
| 4,416,290 A | 11/1983 | Lutkowski |
| 4,425,235 A | 1/1984 | Cornell et al. |
| 4,436,098 A | 3/1984 | Kaufman |
| 4,444,203 A | 4/1984 | Engelman |
| 4,459,997 A | 7/1984 | Sarstedt |
| 4,509,534 A | 4/1985 | Tassin, Jr. |
| 4,608,996 A | 9/1986 | Brown |
| 4,654,027 A | 3/1987 | Dragan et al. |
| 4,657,027 A | 4/1987 | Paulsen |
| 4,657,160 A | 4/1987 | Woods et al. |
| 4,673,386 A | 6/1987 | Gordon |
| 4,676,256 A | 6/1987 | Golden |
| 4,679,571 A | 7/1987 | Frankel et al. |
| 4,705,497 A | 10/1987 | Shitaokoshi et al. |
| 4,714,461 A | 12/1987 | Gabel |
| 4,715,854 A | 12/1987 | Vaillancourt |
| 4,772,273 A | 9/1988 | Alchas |
| 4,820,287 A | 4/1989 | Leonard |
| 4,865,583 A | 9/1989 | Tu |
| 4,879,098 A | 11/1989 | Oberhardt et al. |
| 4,886,072 A | 12/1989 | Percarpio et al. |
| 4,890,627 A | 1/1990 | Haber et al. |
| 4,904,240 A | 2/1990 | Hoover |
| 4,980,297 A | 12/1990 | Haynes et al. |
| 5,027,827 A | 7/1991 | Cody et al. |
| 5,032,116 A | 7/1991 | Peterson et al. |
| 5,045,185 A | 9/1991 | Ohnaka et al. |
| 5,052,403 A * | 10/1991 | Haber .............. A61B 5/150244 600/578 |
| 5,066,284 A | 11/1991 | Mersch et al. |
| 5,084,034 A | 1/1992 | Zanotti |
| 5,097,842 A | 3/1992 | Bonn |
| 5,100,394 A | 3/1992 | Dudar et al. |
| 5,108,927 A | 4/1992 | Dom |
| 5,116,323 A | 5/1992 | Kreuzer et al. |
| 5,122,129 A | 6/1992 | Olson et al. |
| 5,135,489 A | 8/1992 | Jepson et al. |
| 5,222,502 A | 6/1993 | Kurose |
| 5,269,317 A | 12/1993 | Bennett |
| 5,330,464 A | 7/1994 | Mathias et al. |
| 5,360,011 A | 11/1994 | McCallister |
| 5,395,339 A | 3/1995 | Talonn et al. |
| 5,417,673 A | 5/1995 | Gordon |
| 5,429,610 A | 7/1995 | Vaillancourt |
| 5,431,811 A | 7/1995 | Tusini et al. |
| 5,439,450 A | 8/1995 | Haedt |
| 5,450,856 A | 9/1995 | Norris |
| 5,454,786 A | 10/1995 | Harris |
| 5,466,228 A | 11/1995 | Evans |
| 5,472,605 A | 12/1995 | Zuk, Jr. |
| 5,485,854 A | 1/1996 | Hollister |
| 5,507,299 A | 4/1996 | Roland |
| 5,520,193 A | 5/1996 | Suzuki et al. |
| 5,522,804 A | 6/1996 | Lynn |
| 5,575,777 A | 11/1996 | Cover et al. |
| 5,577,513 A | 11/1996 | Van Vlasselaer |
| 5,603,700 A | 2/1997 | Daneshvar |
| 5,632,906 A | 5/1997 | Ishida et al. |

(56) References Cited

U.S. PATENT DOCUMENTS

| | | |
|---|---|---|
| 5,649,912 A | 7/1997 | Peterson |
| 5,691,486 A | 11/1997 | Behringer et al. |
| 5,749,857 A | 5/1998 | Cuppy |
| 5,762,633 A | 6/1998 | Whisson |
| 5,772,608 A | 6/1998 | Dhas |
| 5,785,682 A | 7/1998 | Grabenkort |
| 5,811,658 A | 9/1998 | Van Driel et al. |
| 5,824,001 A | 10/1998 | Erskine |
| 5,865,812 A | 2/1999 | Correia |
| 5,871,699 A | 2/1999 | Ruggeri |
| 5,882,318 A | 3/1999 | Boyde |
| 5,911,705 A | 6/1999 | Howell |
| 5,922,551 A | 7/1999 | Durbin et al. |
| 5,961,472 A | 10/1999 | Swendson et al. |
| 5,971,956 A | 10/1999 | Epstein |
| 5,980,830 A | 11/1999 | Savage et al. |
| 6,001,307 A | 12/1999 | Naka et al. |
| 6,010,633 A | 1/2000 | Zuk, Jr. et al. |
| 6,016,712 A | 1/2000 | Warden et al. |
| 6,050,957 A * | 4/2000 | Desch .............. A61B 5/150244 604/218 |
| 6,106,509 A | 8/2000 | Loubser |
| 6,126,643 A | 10/2000 | Vaillancourt |
| 6,159,164 A | 12/2000 | Neese et al. |
| 6,210,909 B1 | 4/2001 | Guirguis |
| 6,224,561 B1 | 5/2001 | Swendson et al. |
| 6,254,581 B1 | 7/2001 | Scott |
| 6,299,131 B1 | 10/2001 | Ryan |
| 6,325,975 B1 | 12/2001 | Naka et al. |
| 6,328,726 B1 | 12/2001 | Ishida et al. |
| 6,355,023 B1 | 3/2002 | Roth et al. |
| 6,364,890 B1 | 4/2002 | Lum et al. |
| 6,368,306 B1 | 4/2002 | Koska |
| 6,387,086 B2 | 5/2002 | Mathias et al. |
| 6,398,743 B1 | 6/2002 | Halseth |
| 6,403,381 B1 | 6/2002 | Mann et al. |
| 6,478,775 B1 | 11/2002 | Galt et al. |
| 6,506,182 B2 | 1/2003 | Estabrook et al. |
| 6,511,439 B1 | 1/2003 | Tabata et al. |
| 6,520,948 B1 | 2/2003 | Mathias et al. |
| 6,569,117 B1 | 5/2003 | Ziv et al. |
| 6,592,555 B1 | 7/2003 | Wen-Pi |
| 6,626,884 B1 | 9/2003 | Dillon et al. |
| 6,638,252 B2 | 10/2003 | Moulton et al. |
| 6,648,835 B1 | 11/2003 | Shemesh |
| 6,692,479 B2 | 2/2004 | Kraus et al. |
| 6,695,004 B1 | 2/2004 | Raybuck |
| 6,716,187 B1 | 4/2004 | Jorgensen et al. |
| 6,733,433 B1 | 5/2004 | Fell |
| 6,736,783 B2 | 5/2004 | Blake et al. |
| 6,746,420 B1 | 6/2004 | Prestidge et al. |
| 6,843,775 B2 | 1/2005 | Hyun |
| 6,860,871 B2 | 3/2005 | Kuracina et al. |
| 6,905,483 B2 | 6/2005 | Newby et al. |
| 6,913,580 B2 | 7/2005 | Stone |
| 6,945,948 B2 | 9/2005 | Bainbridge et al. |
| 7,044,941 B2 | 5/2006 | Mathias et al. |
| 7,052,603 B2 | 5/2006 | Schick |
| 7,055,401 B2 | 6/2006 | Prybella et al. |
| 7,087,047 B2 | 8/2006 | Kraus et al. |
| 7,141,097 B2 | 11/2006 | Leahey |
| 7,241,281 B2 | 7/2007 | Coelho et al. |
| 7,306,736 B2 | 12/2007 | Collins et al. |
| 7,314,452 B2 | 1/2008 | Madonia |
| 7,316,662 B2 | 1/2008 | Delnevo et al. |
| 7,335,188 B2 | 2/2008 | Graf |
| 7,351,228 B2 | 4/2008 | Keane et al. |
| 7,384,416 B2 | 6/2008 | Goudaliez et al. |
| 7,461,671 B2 | 12/2008 | Ehwald et al. |
| 7,479,131 B2 | 1/2009 | Mathias et al. |
| 7,614,857 B2 | 11/2009 | Fuechslin et al. |
| 7,615,033 B2 | 11/2009 | Leong |
| 7,618,407 B2 | 11/2009 | Demay et al. |
| 7,648,491 B2 | 1/2010 | Rogers |
| 7,666,166 B1 | 2/2010 | Emmert et al. |
| 7,744,573 B2 | 6/2010 | Gordon et al. |
| 7,766,879 B2 | 8/2010 | Tan et al. |
| 8,070,725 B2 | 12/2011 | Christensen |
| 8,197,420 B2 | 6/2012 | Patton |
| 8,231,546 B2 | 7/2012 | Patton |
| 8,282,605 B2 | 10/2012 | Tan et al. |
| 8,287,499 B2 | 10/2012 | Miyasaka |
| 8,337,418 B2 | 12/2012 | Patton |
| 8,349,254 B2 | 1/2013 | Hoshino et al. |
| 8,377,040 B2 | 2/2013 | Burkholz et al. |
| 8,382,712 B2 | 2/2013 | Kim |
| 8,383,044 B2 | 2/2013 | Davis et al. |
| 8,412,300 B2 | 4/2013 | Sonderegger |
| 8,523,826 B2 | 9/2013 | Layton, Jr. |
| 8,535,241 B2 | 9/2013 | Bullington et al. |
| 8,540,663 B2 | 9/2013 | Davey et al. |
| 8,568,371 B2 | 10/2013 | Siopes et al. |
| 8,574,203 B2 | 11/2013 | Stout et al. |
| 8,603,009 B2 | 12/2013 | Tan et al. |
| 8,647,286 B2 | 2/2014 | Patton |
| 8,795,198 B2 | 8/2014 | Tan et al. |
| 8,827,958 B2 | 9/2014 | Bierman et al. |
| 8,864,684 B2 | 10/2014 | Bullington et al. |
| 8,876,734 B2 | 11/2014 | Patton |
| 9,003,879 B1 | 4/2015 | Honan et al. |
| 9,022,950 B2 | 5/2015 | Bullington et al. |
| 9,022,951 B2 | 5/2015 | Bullington et al. |
| 9,060,724 B2 | 6/2015 | Bullington et al. |
| 9,060,725 B2 | 6/2015 | Bullington et al. |
| 9,138,572 B2 | 9/2015 | Zeytoonian et al. |
| 9,155,495 B2 | 10/2015 | Bullington et al. |
| 9,204,864 B2 | 12/2015 | Bullington et al. |
| 9,314,201 B2 | 4/2016 | Burkholz et al. |
| 9,855,386 B2 | 1/2018 | Close et al. |
| 9,895,092 B2 | 2/2018 | Burkholz |
| 9,980,878 B2 | 5/2018 | Marici et al. |
| 9,999,383 B2 | 6/2018 | Bullington et al. |
| 10,086,142 B2 | 10/2018 | Tekeste |
| 10,206,613 B2 | 2/2019 | Bullington et al. |
| 10,219,982 B2 | 3/2019 | Weir et al. |
| 10,251,590 B2 | 4/2019 | Bullington et al. |
| 10,292,633 B2 | 5/2019 | Bullington et al. |
| 10,299,713 B2 | 5/2019 | Patton |
| 10,772,548 B2 | 9/2020 | Bullington et al. |
| 2002/0002349 A1 | 1/2002 | Flaherty et al. |
| 2002/0004647 A1 | 1/2002 | Leong |
| 2002/0183651 A1 | 12/2002 | Hyun |
| 2002/0193751 A1 | 12/2002 | Theeuwes et al. |
| 2003/0013991 A1 | 1/2003 | Stone |
| 2003/0055381 A1 | 3/2003 | Wilkinson |
| 2003/0069543 A1 | 4/2003 | Carpenter et al. |
| 2003/0105414 A1 | 6/2003 | Leong |
| 2003/0208151 A1 | 11/2003 | Kraus et al. |
| 2004/0009542 A1 | 1/2004 | Dumont et al. |
| 2004/0010228 A1 | 1/2004 | Swenson et al. |
| 2004/0054283 A1 | 3/2004 | Corey et al. |
| 2004/0054333 A1 | 3/2004 | Theeuwes et al. |
| 2004/0127816 A1 | 7/2004 | Galvao |
| 2004/0147855 A1 | 7/2004 | Marsden |
| 2005/0004524 A1 | 1/2005 | Newby et al. |
| 2005/0148993 A1 | 7/2005 | Mathias et al. |
| 2005/0154368 A1 | 7/2005 | Lim et al. |
| 2005/0161112 A1 | 7/2005 | Ehwald et al. |
| 2005/0199077 A1 | 9/2005 | Prybella et al. |
| 2005/0240161 A1 | 10/2005 | Crawford |
| 2005/0245885 A1 | 11/2005 | Brown |
| 2005/0273019 A1 | 12/2005 | Conway et al. |
| 2005/0281713 A1 | 12/2005 | Hampsch et al. |
| 2006/0155212 A1 | 7/2006 | Madonia |
| 2006/0251622 A1 | 11/2006 | Suzuki et al. |
| 2006/0287639 A1 | 12/2006 | Sharp |
| 2007/0083162 A1 | 4/2007 | O'Reagan et al. |
| 2007/0088279 A1 | 4/2007 | Shue et al. |
| 2007/0100250 A1 | 5/2007 | Kline |
| 2007/0119508 A1 | 5/2007 | West et al. |
| 2007/0287948 A1 | 12/2007 | Sakiewicz |
| 2008/0086085 A1 | 4/2008 | Brown |
| 2008/0108954 A1 | 5/2008 | Mathias et al. |
| 2008/0167577 A1 | 7/2008 | Weilbacher et al. |

(56) References Cited

U.S. PATENT DOCUMENTS

| | | | |
|---|---|---|---|
| 2008/0200837 | A1 | 8/2008 | Frazier et al. |
| 2008/0254471 | A1 | 10/2008 | Bordano |
| 2008/0255523 | A1 | 10/2008 | Grinberg |
| 2008/0319346 | A1 | 12/2008 | Crawford et al. |
| 2009/0192447 | A1 | 7/2009 | Andersen et al. |
| 2009/0301317 | A1* | 12/2009 | Andrews ............. A23C 3/045 99/453 |
| 2009/0306601 | A1 | 12/2009 | Shaw et al. |
| 2010/0010372 | A1 | 1/2010 | Brown et al. |
| 2010/0042048 | A1 | 2/2010 | Christensen |
| 2010/0057004 | A1 | 3/2010 | Christensen et al. |
| 2010/0094171 | A1 | 4/2010 | Conway et al. |
| 2010/0152681 | A1 | 6/2010 | Mathias |
| 2010/0268118 | A1 | 10/2010 | Schweiger |
| 2010/0286513 | A1 | 11/2010 | Pollard et al. |
| 2011/0306899 | A1 | 12/2011 | Brown et al. |
| 2012/0016266 | A1 | 1/2012 | Burkholz |
| 2012/0022404 | A1 | 1/2012 | Fojtik |
| 2012/0035540 | A1 | 2/2012 | Ferren et al. |
| 2012/0265099 | A1 | 10/2012 | Goodnow, II et al. |
| 2012/0265128 | A1 | 10/2012 | Kolln |
| 2013/0158506 | A1 | 6/2013 | Harris et al. |
| 2014/0066880 | A1 | 3/2014 | Prince et al. |
| 2014/0124542 | A1 | 5/2014 | Kojima et al. |
| 2015/0018715 | A1 | 1/2015 | Walterspiel |
| 2016/0113560 | A1 | 4/2016 | Bullington et al. |
| 2016/0174888 | A1 | 6/2016 | Berthier et al. |
| 2017/0071519 | A1 | 3/2017 | Gelfand et al. |
| 2019/0150818 | A1 | 5/2019 | Bullington et al. |
| 2021/0353193 | A1* | 11/2021 | Bullington ......... A61B 5/15003 |

FOREIGN PATENT DOCUMENTS

| | | |
|---|---|---|
| CN | 101309641 A | 11/2008 |
| CN | 101352357 A | 1/2009 |
| CN | 101437450 A | 5/2009 |
| CN | 101676001 A | 3/2010 |
| CN | 101801445 A | 8/2010 |
| CN | 103027727 A | 4/2013 |
| CN | 105090005 A | 11/2015 |
| CN | 105612346 A | 5/2016 |
| DE | 2 203 858 B2 | 5/1973 |
| DE | 2 541 494 A1 | 3/1977 |
| DE | 299 13 417 U1 | 12/2000 |
| DE | 100 38 026 A1 | 2/2001 |
| DE | 102 43 129 A1 | 4/2004 |
| EP | 0 207 304 A1 | 1/1987 |
| EP | 0 448 795 | 10/1991 |
| EP | 1 980 204 | 10/2008 |
| FR | 2 110 516 A5 | 6/1972 |
| JP | S64-58241 A | 3/1989 |
| JP | 07-016219 A | 1/1995 |
| JP | 2008-149076 A | 7/2008 |
| WO | WO 1990/004351 | 5/1990 |
| WO | WO 1991/018632 | 12/1991 |
| WO | WO 1992/016144 | 10/1992 |
| WO | WO 1995/016395 | 6/1995 |
| WO | WO 1997/018845 | 5/1997 |
| WO | WO 1998/046136 | 10/1998 |
| WO | WO 1999/013925 | 3/1999 |
| WO | WO 1999/048425 | 9/1999 |
| WO | WO 1999/055232 | 11/1999 |
| WO | WO 2000/041624 | 7/2000 |
| WO | WO 2001/008546 | 2/2001 |
| WO | WO 2002/051520 | 7/2002 |
| WO | WO 2003/008012 | 1/2003 |
| WO | WO 2005/068011 | 7/2005 |
| WO | WO 2006/031500 | 3/2006 |
| WO | WO 2007/033319 | 3/2007 |
| WO | WO 2008/101025 | 8/2008 |
| WO | WO 2011/069145 | 6/2011 |
| WO | WO 2012/012127 | 1/2012 |
| WO | WO 2014/022750 | 2/2014 |
| WO | WO 2014/085800 | 6/2014 |
| WO | WO 2016/054252 | 4/2016 |

OTHER PUBLICATIONS

Office Action for U.S. Appl. No. 11/955,635, dated Dec. 3, 2010, 11 pages.
Office Action for U.S. Appl. No. 13/335,241, dated Apr. 20, 2012, 12 pages.
Office Action for U.S. Appl. No. 13/458,508, dated Jul. 24, 2012, 13 pages.
Office Action for U.S. Appl. No. 13/675,295, dated May 23, 2013, 15 pages.
Office Action for U.S. Appl. No. 14/089,267, dated Jun. 19, 2014, 13 pages.
Office Action for U.S. Appl. No. 14/498,102, dated Oct. 17, 2017, 20 pages.
Office Action for U.S. Appl. No. 14/498,102, dated Sep. 24, 2018, 18 pages.
Office Action for U.S. Appl. No. 15/088,842, dated Nov. 23, 2016, 20 pages.
Office Action for U.S. Appl. No. 15/432,310, dated Apr. 12, 2017, 14 pages.
Office Action for U.S. Appl. No. 15/435,684, dated Jun. 12, 2017, 19 pages.
Office Action for U.S. Appl. No. 15/448,891, dated Jun. 16, 2017, 25 pages.
Office Action for U.S. Appl. No. 15/457,082, dated Jun. 15, 2017, 22 pages.
Office Action for U.S. Appl. No. 15/829,015, dated Feb. 6, 2018, 24 pages.
Office Action for U.S. Appl. No. 15/829,018, dated Feb. 16, 2018, 13 pages.
Office Action for U.S. Appl. No. 15/829,023, dated Feb. 7, 2018, 25 pages.
Office Action for U.S. Appl. No. 15/832,055, dated Feb. 8, 2018, 21 pages.
Office Action for U.S. Appl. No. 15/832,087, dated Feb. 7, 2018, 24 pages.
Office Action for U.S. Appl. No. 13/954,528, dated Mar. 17, 2014, 10 pages.
Office Action for U.S. Appl. No. 15/832,091, dated Feb. 22, 2018, 16 pages.
Office Action for U.S. Appl. No. 16/299,962, dated May 2, 2019, 14 pages.
Office Action for U.S. Appl. No. 16/299,962, dated Dec. 9, 2020, 15 pages.
Office Action for U.S. Appl. No. 16/299,962, dated Jun. 15, 2021, 17 pages.
Office Action for U.S. Appl. No. 14/493,796, dated Jan. 27, 2015, 7 pages.
Office Action for U.S. Appl. No. 14/494,208, dated Jan. 27, 2015, 7 pages.
Office Action for U.S. Appl. No. 14/662,676, dated Sep. 5, 2018, 25 pages.
Office Action for U.S. Appl. No. 14/712,437 dated Oct. 25, 2018, 20 pages.
Office Action for U.S. Appl. No. 15/854,273, dated Sep. 7, 2018, 15 pages.
Office Action for U.S. Appl. No. 15/854,273, dated Jan. 13, 2020, 13 pages.
Office Action for U.S. Appl. No. 16/376,745, dated May 14, 2021, 13 pages.
Office Action for U.S. Appl. No. 16/255,055, dated Mar. 18, 2019, 16 pages.
Office Action for U.S. Appl. No. 13/952,964, dated Mar. 20, 2015, 11 pages.
Office Action for U.S. Appl. No. 14/926,784, dated May 25, 2018, 15 pages.
Office Action for U.S. Appl. No. 14/926,784, dated Jan. 15, 2019, 15 pages.

(56) References Cited

OTHER PUBLICATIONS

Office Action for U.S. Appl. No. 14/926,784, dated Jan. 21, 2020, 17 pages.
Office Action for U.S. Appl. No. 14/264,481, dated Jul. 1, 2015, 13 pages.
Office Action for U.S. Appl. No. 14/264,481, dated Feb. 26, 2016, 10 pages.
Office Action for U.S. Appl. No. 14/264,481, dated Jul. 14, 2016, 9 pages.
Office Action for U.S. Appl. No. 14/264,481, dated Oct. 21, 2016, 10 pages.
Office Action for U.S. Appl. No. 14/264,481, dated Apr. 13, 2017, 14 pages.
Office Action for U.S. Appl. No. 14/264,481, dated Sep. 7, 2017, 12 pages.
Office Action for U.S. Appl. No. 14/880,397, dated Apr. 17, 2018, 6 pages.
Office Action for U.S. Appl. No. 14/880,397, dated Sep. 24, 2018, 5 pages.
Office Action for U.S. Appl. No. 16/255,058, dated Mar. 30, 2021, 16 pages.
International Search Report and Written Opinion for International Application No. PCT/US2007/087951, dated May 16, 2008, 8 pages.
Examination Report for United Kingdom Application No. GB1805101.1, dated May 25, 2018, 8 pages.
International Search Report and Written Opinion for International Application No. PCT/US2013/071491, dated Aug. 5, 2014, 9 pages.
Notification of the First Office Action for Chinese Application No. 201380040468.7, dated Jun. 30, 2016, 9 pages.
Supplementary European Search Report for EP Application No. 13797732.8, dated Dec. 7, 2015, 5 pages.
International Search Report and Written Opinion for International Application No. PCT/US2013/043289, dated Oct. 24, 2013, 15 pages.
International Search Report and Written Opinion for International Application No. PCT/US2013/052493, dated Nov. 27, 2013, 7 pages.
Notification of the First Office Action for Chinese Application No. 201380071681.4, dated Aug. 16, 2016, 9 pages.
Notification of the Second Office Action for Chinese Application No. 201380071681.4, dated Jun. 28, 2017, 9 pages.
Extended European Search Report for EP Application No. 13859067.4, dated Jun. 7, 2016, 4 pages.
Extended European Search Report for EP Application No. 13859067.4, dated Jan. 27, 2017, 4 pages.
Extended European Search Report for EP Application No. 13859067.4, dated Aug. 16, 2017, 6 pages.
Extended European Search Report for EP Application No. 18188136.8, dated May 16, 2019, 9 pages.
Notice of Reasons for Rejection for Japanese Application No. 2018-081980, dated Feb. 21, 2019, 9 pages.
International Search Report and Written Opinion for International Application No. PCT/US2013/072563, dated Feb. 7, 2014, 11 pages.
Arkin, C. F. et al., "Procedures for the Collection of Diagnostic Blood Specimens by Venipuncture; Approved Standard," Fifth Edition, Clinical and Laboratory Standards Institute, vol. 23, No. 32 (2003), 52 pages.
Barnard, D. R. & Arthur, M. M., "Fibronectin (cold insoluble globulin) in the neonate," Clinical and Laboratory Observations, 102(3): 453-455 (1983).
Baxter, "IV Tubing and Access Devices" authored by and published by Baxter, dated Nov. 6, 2006, 105 pages.
BD Saf-T-Intima Closed IV Catheter System, Becton, Dickinson and Company, 2015 Brochure. Retrieved from the Internet (Sep. 11, 2019) <https://www.bd.com/en-us/offerings/capabilities/infusion-therapy/iv-catheters/bd-saf-tintima-closed-iv-catheter-system>, 2 pages.
BD Vacutainer Passive Shielding Blood Collection Needle Brochure; Becton Dickinson and Company (2005), 2 pages.
Brecher, M. E. et al., "Bacterial Contamination of Blood Components," Clinical Microbiology Reviews, 18(1):195-204 (2005).
Calam, R. R., "Recommended 'Order of Draw' for Collecting Blood Specimens Into Additive-Containing Tubes," Letter to the Editor, Clinical Chemistry, 28(6):1399 (1982), 1 page.
Cartridge and Test Information, Abbott, Art: 714258-01O Rev. Date: Aug. 15-16, 6 pages.
Challiner, A. et al., Queen Alexandra Hospital, Portsmouth P06 3LY, "Venous/arterial blood management protection system," Correspondence, p. 169.
De Korte, D. et al., "Diversion of first blood volume results in a reduction of bacterial contamination for whole-blood collections," Vox Sanguinis, 83:13-16 (2002).
De Korte, D. et al., "Effects of skin disinfection method, deviation bag, and bacterial screening on clinical safety of platelet transfusions in the Netherlands," Transfusion, 46: 476-485 (2006).
Edwards Lifesciences, "Conservation. Safety. Simplicity. Edwards VAMP and VAMP Jr. Systems," 2002 Brochure. Retrieved from the Internet (Sep. 11, 2019) <https://www.medline.com/media/catalog/Docs/MKT/VAMPSYSTEMBROCHURE.PDF>, 4 pages.
Ernst, D. J. et al., "NCCLS simplifies the order of draw: a brief history," MLO, 26-27 (2004).
Gottlieb, T., "Hazards of Bacterial Contamination of Blood Products," Anaesth Intens Care, 21: 20-23 (1993).
Hall, K. K. et al., "Updated Review of Blood Culture Contamination," Clinical Microbiology Reviews, 19(4):788-802 (2006).
Hillyer, C. D. et al., "Bacterial Contamination of Blood Components Risks, Strategies, and Regulation," Hematology, 575-589 (2003).
Kim, J. Y. et al., "The Sum of the Parts is Greater Than the Whole: Reducing Blood Culture Contamination," Annals of Internal Medicine, 154:202-203 (2011).
Levin, P. D. et al., "Use of the Nonwire Central Line Hub to Reduce Blood Culture Contamination," Chest, 143(3):640-645 (2013).
Pall Corp., "Leukotrap Filtration Systems for Whole Blood Derived Platelets: Leukotrap RC PL and Leukotrap PL Systems," 2005 Brochure, 2 pages.
Li, Y. et al., "Direct labeling and visualization of blood vessels with lipophilic carbocyanine dye DiI," Nature Protocols, 3(11): 1703-1708 (2008).
Liumbruno, G. M. et al., "Reduction of the risk of bacterial contamination of blood components through diversion of the first part of the donation of blood and blood components," Blood Transfus, 7: 86-93 (2009).
Mayer, G. A., "A Method for the Reliable Determination of Clotting Time in Whole Blood," Can Med Assoc J., 72(12): 927-929 (1955).
McDonald, C. P., "Interventions Implemented to Reduce the Risk of Transmission of Bacteria by Transfusion in the English National Blood Service," Transfus Med Hemother, 38:255-258 (2011).
Meissner, G. F. et al., "A Method Based on the Use of Whole Venous Blood in Capillary Tubes," American Journal of Clinical Pathology, 33(2): 29-31 (1963).
Murphy, M., "Better Blood Transfusion," Journal of the Intensive Core Society, 4(3): 78-80 (2003).
Napolitano, M et al., "Quality control of bacterial contamination of blood components: the feasibility of diversion system testing," Blood Transfus, 2: 231-232 (2004).
Norberg, A. et al., "Contamination Rates of Blood Cultures Obtained by Dedicated Phlebotomy vs Intravenous Catheter," JAMA, 289(6): 726-729 (2003).
Order of Draw for Multiple Tube Collections, LabNotes, a newsletter from BD Diagnostics,—Preanalytical Systems, 17(1):3 (2007).
Page, C. et al., "Blood conservation devices in critical care: a narrative review," Annals of Intensive Care, 3:14 (2013), 6 pages.
Palavecino, E. L. et al., "Detecting Bacterial Contamination in Platelet Products," Clin. Lab., 52:443-456 (2006).
Patton, R. G. et al., "Innovation for Reducing Blood Culture Contamination: Initial Specimen Diversion Technique," Journal of Clinical Microbiology, 48(12):4501-4503 (2010).
Perez, P. et al., "Multivariate analysis of determinants of bacterial contamination of whole-blood donations," Vox Sanguinis, 82:55-60 (2002).

(56) References Cited

OTHER PUBLICATIONS

Proehl, J. A. et al., "Clinical Practice Guideline: Prevention of Blood Culture Contamination, Full Version," 2012 ENA Emergency Nurses Resources Development Committee, Emergency Nurses Association (Dec. 2012), 14 pages.
Quilici, N. et al., "Differential Quantitative Blood Cultures in the Diagnosis of Catheter-Related Sepsis in Intensive Care Units," Clinical Infectious Diseases 25:1066-1070 (1997).
Schuur, J., "Blood Cultures: When Do they Help and When Do They Harm?" Brigham & Women's Hospital, Department of Emergency Medicine, (Jun. 21-23, 2012), 42 pages.
Sheppard, C. A. et al., "Bacterial Contamination of Platelets for Transfusion: Recent Advances and Issues," LabMedicine, 36(12):767-770 (2005).
Shulman, G., "Quality of Processed Blood for Autotransfusion," The Journal of Extra-Corporeal Technology, 32(1): 11-19 (2000).
Sibley, C. D. et al., "Molecular Methods for Pathogen and Microbial Community Detection and Characterization: Current and Potential Application in Diagnostic Microbiology," Infection, Genetics and Evolution 12:505-521 (2012).
Stohl, S. et al., "Blood Cultures at Central Line Insertion in the Intensive Care Unit: Comparison with Peripheral Venipuncture," Journal of Clinical Microbiology, 49(7):2398-2403 (2011).
Tang, M. et al., "Closed Blood Conservation Device for Reducing Catheter-Related Infections in Children After Cardiac Surgery," Critical Care Nurse, 34(5): 53-61 (2014).
Wagner et al., "Diversion of Initial Blood Flow to Prevent Whole-Blood Contamination by Skin Surface Bacteria: an in vitro model," Transfusion, 40:335-338 (2000).
Wang, P. et al., "Strategies on Reducing Blood Culture Contamination," Reviews in Medical Microbiology, 23:63-66 (2012).
Weinbaum, F. I. et al., "Doing it Right the First Time: Quality Improvement and the Contaminant Blood Culture," Journal of Clinical Microbiology, 35(3): 563-565 (1997).
Weinstein, M. P., "Current Blood Culture Methods and Systems: Clinical Concepts, Technology, and Interpretation of Results," Clinical Infectious Diseases, 23: 40-46 (1996).
Weinstein, M. P., "MiniReview: Blood Culture Contamination: Persisting Problems and Partial Progress," Journal of Clinical Microbiology, 41(6): 2275-2278 (2003).
Weinstein, M. P. et al., "The Clinical Significance of Positive Blood Cultures in the 1990s: A Prospective Comprehensive Evaluation of the Microbiology, Epidemiology, and Outcome of Bacteremia and Fungemia in Adults," Clinical Infectious Diseases, 24:584-602 (1997).
Ziegler, et al., "Controlled Clinical Laboratory Comparison of Two Supplemented Aerobic and Anaerobic Media Used in Automated Blood Culture Systems to Detect Bloodstream Infections," J. Clinical Microbiology, 36(3):657-661 (1998).
Zimmon, D. S. et al., "Effect of Portal Venous Blood Flow Diversion on Portal Pressure," J Clin Invest, 65(6): 1388-1397 (1980).
Zundert, A. V., "New Closed IV Catheter System," Acta Anaesth. Belg., 56: 283-285 (2005).
Exhibit 01—Defendant's Invalidity Contentions, Invalidity Claim Chart—U.S. Pat. No. 9,855,001 vs Barnard NPL, Aug. 30, 2019, 8 pages.
Exhibit 02—Defendant's Invalidity Contentions, Invalidity Claim Chart—U.S. Pat. No. 9,855,001 vs BD Needle NPL, Aug. 30, 2019, 7 pages.
Exhibit 03—Defendant's Invalidity Contentions, Invalidity Claim Chart—U.S. Pat. No. 9,855,001 vs U.S. Pat. No. 6,626,884, Aug. 30, 2019, 11 pages.
Exhibit 04—Defendant's Invalidity Contentions, Invalidity Claim Chart—U.S. Pat. No. 9,855,001 vs U.S. Pat. Pub. No. 2005/161112, Aug. 30, 2019, 22 pages.
Exhibit 05—Defendant's Invalidity Contentions, Invalidity Claim Chart—U.S. Pat. No. 9,855,001 vs U.S. Pat. No. 4,673,386, Aug. 30, 2019, 21 pages.
Exhibit 06—Defendant's Invalidity Contentions, Invalidity Claim Chart—U.S. Pat. No. 9,855,001 vs U.S. Pat. No. 4,904,240, Aug. 30, 2019, 15 pages.
Exhibit 07—Defendant's Invalidity Contentions, Invalidity Claim Chart—U.S. Pat. No. 9,855,001 vs Leukotrap NPL, Aug. 30, 2019, 38 pages.
Exhibit 09—Defendant's Invalidity Contentions, Invalidity Claim Chart—U.S. Pat. No. 9,855,001 vs U.S. Pat. No. 4,106,497, Aug. 30, 2019, 22 pages.
Exhibit 10—Defendant's Invalidity Contentions, Invalidity Claim Chart—U.S. Pat. No. 9,855,001 vs Stopcock-Syringe NPL, Aug. 30, 2019, 85 pages.
Exhibit 11—Defendant's Invalidity Contentions, Invalidity Claim Chart—U.S. Pat. No. 9,855,001 vs Ziegler NPL, Aug. 30, 2019, 8 pages.
Exhibit 12—Defendant's Invalidity Contentions, Invalidity Claim Chart—U.S. Pat. No. 10,028,689 vs Barnard NPL, Aug. 30, 2019, 12 pages.
Exhibit 13—Defendant's Invalidity Contentions, Invalidity Claim Chart—U.S. Pat. No. 10,028,689 vs U.S. Pat. No. 6,626,884, Aug. 30, 2019, 29 pages.
Exhibit 14—Defendant's Invalidity Contentions, Invalidity Claim Chart—U.S. Pat. No. 10,028,689 vs U.S. Pat. Pub. No. 2005/161112, Aug. 30, 2019, 48 pages.
Exhibit 15—Defendant's Invalidity Contentions, Invalidity Claim Chart—U.S. Pat. No. 10,028,689 vs U.S. Pat. No. 4,673,386, Aug. 30, 2019, 44 pages.
Exhibit 16—Defendant's Invalidity Contentions, Invalidity Claim Chart—U.S. Pat. No. 10,028,689 vs U.S. Pat. No. 4,904,240, Aug. 30, 2019, 31 pages.
Exhibit 17—Defendant's Invalidity Contentions, Invalidity Claim Chart—U.S. Pat. No. 10,028,689 vs Leukotrap NPL, Aug. 30, 2019, 113 pages.
Exhibit 19—Defendant's Invalidity Contentions, Invalidity Claim Chart—U.S. Pat. No. 10,028,689 vs U.S. Pat. No. 4,106,497, Aug. 30, 2019, 38 pages.
Exhibit 20—Defendant's Invalidity Contentions, Invalidity Claim Chart—U.S. Pat. No. 10,028,689 vs Stopcock-Syringe NPL, Aug. 30, 2019, 268 pages.
Exhibit 21—Defendant's Invalidity Contentions, Invalidity Claim Chart—U.S. Pat. No. 10,220,139 vs U.S. Pat. No. 6,626,884, Aug. 30, 2019, 35 pages.
Exhibit 22—Defendant's Invalidity Contentions, Invalidity Claim Chart—U.S. Pat. No. 10,220,139 vs U.S. Pat. Pub. No. 2005/161112, Aug. 30, 2019, 46 pages.
Exhibit 23—Defendant's Invalidity Contentions, Invalidity Claim Chart—U.S. Pat. No. 10,220,139 vs U.S. Pat. No. 4,207,870, Aug. 30, 2019, 20 pages.
Exhibit 24—Defendant's Invalidity Contentions, Invalidity Claim Chart—U.S. Pat. No. 10,220,139 vs U.S. Pat. No. 6,506,182, Aug. 30, 2019, 15 pages.
Exhibit 25—Defendant's Invalidity Contentions, Invalidity Claim Chart—U.S. Pat. No. 10,220,139 vs U.S. Pat. No. 4,673,386, Aug. 30, 2019, 53 pages.
Exhibit 26—Defendant's Invalidity Contentions, Invalidity Claim Chart—U.S. Pat. No. 10,220,139 vs U.S. Pat. No. 4,904,240, Aug. 30, 2019, 39 pages.
Exhibit 27—Defendant's Invalidity Contentions, Invalidity Claim Chart—U.S. Pat. No. 10,220,139 vs Leukotrap NPL, Aug. 30, 2019, 115 pages.
Exhibit 29—Defendant's Invalidity Contentions, Invalidity Claim Chart—U.S. Pat. No. 10,220,139 vs U.S. Pat. No. 4,106,497, Aug. 30, 2019, 45 pages.
Exhibit 30—Defendant's Invalidity Contentions, Invalidity Claim Chart—U.S. Pat. No. 10,220,139 vs Stopcock-Syringe NPL, Aug. 30, 2019, 246 pages.
Exhibit 31—Defendant's Invalidity Contentions, Invalidity Claim Chart—U.S. Pat. No. 10,220,139 vs U.S. Pat. No. 4,349,035, Aug. 30, 2019, 26 pages.
Exhibit 32—Defendant's Invalidity Contentions, Invalidity Claim Chart—U.S. Pat. No. 10,220,139 vs U.S. Pat. Pub. No. 2008/0145933A1, Aug. 30, 2019, 39 pages.

(56) References Cited

OTHER PUBLICATIONS

Exhibit 33—Defendant's Invalidity Contentions, Invalidity Claim Chart—U.S. Pat. No. 10,039,483 vs Barnard NPL, Aug. 30, 2019, 14 pages.
Exhibit 34—Defendant's Invalidity Contentions, Invalidity Claim Chart—U.S. Pat. No. 10,039,483 vs U.S. Pat. No. 6,626,884, Aug. 30, 2019, 22 pages.
Exhibit 35—Defendant's Invalidity Contentions, Invalidity Claim Chart—U.S. Pat. No. 10,039,483 vs U.S. Pat. Pub. No. 2005/161112, Aug. 30, 2019, 45 pages.
Exhibit 36—Defendant's Invalidity Contentions, Invalidity Claim Chart—U.S. Pat. No. 10,039,483 vs U.S. Pat. No. 4,673,386, Aug. 30, 2019, 47 pages.
Exhibit 37—Defendant's Invalidity Contentions, Invalidity Claim Chart—U.S. Pat. No. 10,039,483 vs U.S. Pat. No. 4,904,240, Aug. 30, 2019, 30 pages.
Exhibit 38—Defendant's Invalidity Contentions, Invalidity Claim Chart—U.S. Pat. No. 10,039,483 vs Leukotrap NPL, Aug. 30, 2019, 115 pages.
Exhibit 40—Defendant's Invalidity Contentions, Invalidity Claim Chart—U.S. Pat. No. 10,039,483 vs U.S. Pat. No. 4,106,497, Aug. 30, 2019, 45 pages.
Exhibit 41—Defendant's Invalidity Contentions, Invalidity Claim Chart—U.S. Pat. No. 10,039,483 vs Stopcock-Syringe NPL, Aug. 30, 2019, 214 pages.
Exhibit 42—Defendant's Invalidity Contentions, Invalidity Claim Chart—U.S. Pat. No. 10,039,483 vs U.S. Pat. Pub. No. 2008/0145933A1, Aug. 30, 2019, 38 pages.
Office Action for U.S. Appl. No. 17/388,971, dated Nov. 23, 2021, 19 pages.
Notice of Reasons for Rejection for Japanese Application No. 2020-075727, dated Jul. 21, 2021, with English translation, 37 pages.
Extended European Search Report for European Application No. 21167069.0, dated Nov. 10, 2021, 9 pages.
Extended European Search Report for European Application No. 21167625.9, dated Oct. 8, 2021, 7 pages.
Notice of Reasons for Rejection for Japanese Application No. 2020-094488, dated Aug. 2, 2021, 4 pages.
Extended European Search Report dated Aug. 30, 2021 for European Application No. 20207898.6, 8 pages.

\* cited by examiner

SYRINGE-BASED FLUID DIVERSION MECHANISM FOR BODILY FLUID SAMPLING

CROSS-REFERENCE TO RELATED APPLICATIONS

This application is a continuation of U.S. patent application Ser. No. 16/255,058, filed Jan. 23, 2019, entitled "Syringe-Based Fluid Diversion Mechanism for Bodily Fluid Sampling," which is a continuation of U.S. patent application Ser. No. 14/880,397, filed Oct. 12, 2015, now U.S. Pat. No. 10,206,613, entitled "Syringe-Based Fluid Diversion Mechanism for Bodily Fluid Sampling," which is a continuation of U.S. patent application Ser. No. 14/094,073, filed Dec. 2, 2013, now U.S. Pat. No. 9,155,495, entitled "Syringe-Based Fluid Diversion Mechanism for Bodily Fluid Sampling," which claims priority to and the benefit of U.S. Provisional Application Ser. No. 61/731,620, entitled "Syringe Based Fluid Diversion Mechanism for Bodily-Fluid Sampling," filed Nov. 30, 2012, the disclosures of which are incorporated herein by reference in their entireties.

BACKGROUND

Embodiments described herein relate generally to the parenteral procurement of bodily-fluid samples, and more particularly to devices and methods for parenterally-procuring bodily-fluid samples with reduced contamination from microbes or other contaminants exterior to the bodily-fluid source, such as dermally-residing microbes.

Health care practitioners routinely perform various types of microbial tests on patients using parenterally-obtained bodily-fluids. In some instances, patient samples (e.g., bodily-fluids) are tested for the presence of one or more potentially undesirable microbes, such as bacteria, fungi, or yeast (e.g., *Candida*). Microbial testing may include incubating patient samples in one or more sterile vessels containing culture media that is conducive to microbial growth, real-time diagnostics, and/or PCR-based approaches. Generally, when such microbes are present in the patient sample, the microbes flourish over time in the culture medium. After a pre-determined amount of time (e.g., a few hours to several days), the culture medium can be tested for the presence of the microbes. The presence of microbes in the culture medium suggests the presence of the same microbes in the patient sample which, in turn, suggests the presence of the same microbes in the bodily-fluid of the patient from which the sample was obtained. Accordingly, when microbes are determined to be present in the culture medium, the patient may be prescribed one or more antibiotics or other treatments specifically designed to treat or otherwise remove the undesired microbes from the patient.

Patient samples, however, can become contaminated during procurement. One way in which contamination of a patient sample may occur is by the transfer of microbes from a bodily surface (e.g., dermally-residing microbes) dislodged during needle insertion into a patient and subsequently transferred to a culture medium with the patient sample. The bodily surface and/or other undesirable external microbes may be dislodged either directly or via dislodged tissue fragments, hair follicles, sweat glands and other adnexal structures. Another possible source of contamination is from the person drawing the patient sample. For example, a doctor, phlebotomist, nurse, etc. can transfer contaminants from their body (e.g., finger, arms, etc.) to the patient sample. The transferred microbes may thrive in the culture medium and eventually yield a positive microbial test result, thereby falsely indicating the presence of such microbes in vivo. Such inaccurate results are a concern when attempting to diagnose or treat a suspected illness or condition. For example, false positive results from microbial tests may result in the patient being unnecessarily subjected to one or more anti-microbial therapies, which may cause serious side effects to the patient including, for example, death, as well as produce an unnecessary burden and expense to the health care system.

As such, a need exists for improved bodily-fluid transfer devices and methods that reduce microbial contamination in bodily-fluid test samples.

SUMMARY

Devices for parenterally-procuring bodily-fluid samples with reduced contamination from microbes exterior to the bodily-fluid source, such as dermally-residing microbes, are described herein. In some embodiments, a syringe-based device for parenterally-procuring bodily fluid samples with reduced contamination from a patient includes a housing, a pre-sample reservoir, and an actuator mechanism. The housing has a proximal end portion and a distal end portion and defines an inner volume therebetween. The proximal end portion is substantially open and the distal end portion has a port configured to be coupled to a lumen-defining device for receiving bodily fluids from the patient. The pre-sample reservoir is fluidically couplable to the port and is configured to receive and isolate a first volume of bodily fluid withdrawn from the patient. The actuator mechanism is at least partially disposed in the inner volume of the housing and has a proximal end portion and a distal end portion. The distal end portion includes a sealing member and the proximal end portion includes an engagement portion configured to allow a user to selectively move the actuator mechanism between a first configuration in which the bodily fluid can flow from the port to the pre-sample reservoir, and a second configuration in which the bodily fluid can flow from the port to a sample reservoir defined at least in part by the sealing member and the housing.

DETAILED DESCRIPTION

Figure 1:
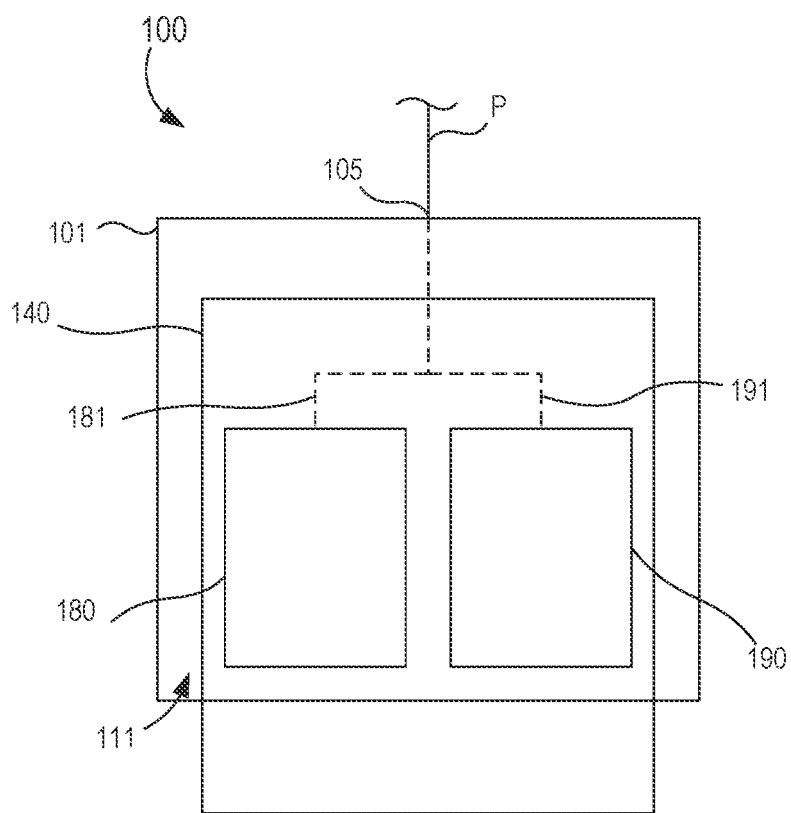
FIG. 1 is a schematic illustration of a syringe-based transfer device according to an embodiment.

Devices for parenterally-procuring bodily-fluid samples with reduced contamination from microbes exterior to the bodily-fluid source, such as dermally-residing microbes, are described herein. In some embodiments, a syringe-based device for parenterally-procuring bodily fluid samples with reduced contamination from a patient includes a housing, a pre-sample reservoir, and an actuator mechanism. The housing has a proximal end portion and a distal end portion and defines an inner volume therebetween. The proximal end portion is substantially open and the distal end portion has a port configured to be coupled to a lumen-defining device for receiving bodily fluids from the patient. The pre-sample reservoir is fluidically couplable to the port and is configured to receive and isolate a first volume of bodily fluid withdrawn from the patient. The actuator mechanism is at least partially disposed in the inner volume of the housing and has a proximal end portion and a distal end portion. The distal end portion includes a sealing member and the proximal end portion includes an engagement portion configured to allow a user to selectively move the actuator mechanism between a first configuration in which the bodily fluid can flow from the port to the pre-sample reservoir, and a second configuration in which the bodily fluid can flow from the port to a sample reservoir defined at least in part by the sealing member and the housing.

In some embodiments, a syringe-based device for parenterally-procuring bodily fluid samples with reduced contamination from a patient includes a housing and an actuator mechanism. The housing has a proximal end portion and a distal end portion and defines an inner volume therebetween. The proximal end portion is substantially open and the distal end portion has a port configured to be coupled to a lumen-defining device for receiving bodily fluids from the patient. The actuator mechanism is movably disposed in the inner volume. The actuator mechanism includes a first member having a proximal end portion and a distal end portion and defining an inner volume therebetween, and a second member movably disposed in the inner volume of the first member. The distal end portion of the first member includes a first plunger including a flow channel configured to allow selective fluid communication between the inner volume defined by the housing and the inner volume defined by the first member. The second member includes a second plunger disposed at a distal end portion of the second member and an engagement portion configured to allow a user to selectively move the actuator mechanism.

In some embodiments, a syringe-based device for parenterally-procuring bodily fluid samples with reduced contamination from a patient includes a housing, an actuator mechanism, and a piercing member. The housing has a proximal end portion and a distal end portion and defines an inner volume therebetween. The proximal end portion is substantially open and the distal end portion has a port configured to be coupled to a lumen-defining device for receiving bodily fluids from the patient. The actuator mechanism is movably disposed in the inner volume of the housing. The actuator mechanism has a proximal end portion and a distal end portion and defining an inner volume therebetween. The distal end portion includes a plunger including a flow channel. The proximal end portion is substantially open and configured to receive a vacuum-sealed sample tube. The piercing member is disposed in the inner volume of the actuator mechanism and defines a lumen fluidically coupled to the flow channel of the plunger. The flow channel of the plunger and the piercing member configured to allow selective fluid communication between the inner volume defined by the housing and the inner volume defined by the actuator mechanism.

In some embodiments, a syringe-based device for parenterally-procuring bodily fluid samples with reduced contamination from a patient includes a housing, an actuator mechanism, and a flow control mechanism. The housing has a proximal end portion and a distal end portion and defines an inner volume therebetween. The proximal end portion is substantially open and the distal end portion has a port configured to be coupled to a lumen-defining device for receiving bodily fluids from the patient. The actuator mechanism is movably disposed in the inner volume of the housing and has a proximal end portion and a distal end portion. The distal end portion includes a first plunger and the proximal end portion including an engagement portion configured to allow a user to selectively move the actuator mechanism. A second plunger is movably disposed in the inner volume of the housing and releasably coupled to the actuator mechanism. The second plunger defines a flow channel configured to be placed in selective fluid communication with the port. The flow control mechanism is operable to selectively control fluid flow between the port and a pre-sample reservoir defined by the second plunger and the housing. The flow control mechanism is configured to be moved between a first configuration in which the bodily fluid can flow through a first flow path to the pre-sample reservoir, and a second configuration in which the bodily fluid can flow through a second flow path to a sample reservoir collectively defined by the first plunger, the second plunger, and the housing.

In some embodiments, a method of using a syringe-based transfer device, including a housing with a port and an actuator mechanism movably disposed in the housing, to obtain a bodily fluid sample from a patient includes establishing fluid communication between the patient and the port of the syringe-based transfer device and establishing fluid communication between the port and a pre-sample reservoir. A first volume of bodily fluid is transferred to the pre-sample reservoir with the syringe-based transfer device. The pre-sample reservoir is fluidically isolated from the port to sequester the first volume of bodily fluid in the pre-sample reservoir. After the first volume of bodily fluid has been sequestered in the pre-sample reservoir, fluid communication is established between the port and a sample reservoir defined at least in part by the actuator mechanism and the housing. The actuator mechanism is moved from a first position to a second position to draw a second volume of bodily fluid from the patient into the sample reservoir.

In some embodiments, an apparatus includes a housing and an actuator mechanism. The apparatus further includes a first fluid reservoir and a second fluid reservoir, fluidically isolated from the first fluid reservoir, defined at least in part by the housing and/or the actuator mechanism. The housing includes a port configured to receive a bodily-fluid. The housing and the actuator mechanism collectively define a first fluid flow path and a second fluid flow path. The first fluid flow path is configured to transfer a first flow of bodily-fluid from the port to the first fluid reservoir when the actuator mechanism is in a first position relative to the housing. The second fluid flow path is configured to transfer a second flow of bodily-fluid, substantially free from undesirable microbes that are not representative of in vivo patient condition, from the port to the second fluid reservoir when the actuator mechanism is in a second position relative to the housing.

In some embodiments, a bodily-fluid transfer device can be configured to selectively divert a first, predetermined amount of a flow of a bodily-fluid to a first reservoir before permitting the flow of a second amount of the bodily-fluid into a second reservoir. In this manner, the second amount of bodily-fluid can be used for diagnostic or other testing, while the first amount of bodily-fluid, which may contain microbes from a bodily surface and/or other external source, is isolated from the bodily-fluid to be tested for microbial presence but yet can be used for other blood tests as ordered by clinician (e.g., complete blood count "CBC", immuno-diagnostic tests, cancer-cell detection tests, or the like).

As referred to herein, "bodily-fluid" can include any fluid obtained from a body of a patient, including, but not limited to, blood, cerebrospinal fluid, urine, bile, lymph, saliva, synovial fluid, serous fluid, pleural fluid, amniotic fluid, and the like, or any combination thereof.

As used herein, the term "set" can refer to multiple features or a singular feature with multiple parts. For example, when referring to set of walls, the set of walls can be considered as one wall with distinct portions, or the set of walls can be considered as multiple walls. Similarly stated, a monolithically constructed item can include a set of walls. Such a set of walls can include, for example, multiple portions that are in discontinuous from each other. A set of walls can also be fabricated from multiple items that are produced separately and are later joined together (e.g., via a weld, an adhesive or any suitable method).

As used in this specification, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used in this specification and the appended claims, the terms "first, predetermined amount," "first amount," and "first volume" describe an amount of bodily-fluid configured to be received or contained by a first reservoir or a pre-sample reservoir. While the terms "first amount" and "first volume" do not explicitly describe a predetermined amount, it should be understood that the first amount is the first, predetermined amount unless explicitly described differently.

As used in this specification and the appended claims, the terms "second amount" and "second volume" describe an amount of bodily-fluid configured to be received or contained by a second reservoir or sample reservoir. The second amount can be any suitable amount of bodily-fluid and need not be predetermined. Conversely, when explicitly described as such, the second amount received and contained by the second reservoir or sample reservoir can be a second, predetermined amount.

FIG. 1 is a schematic illustration of a portion of a syringe-based transfer device 100, according to an embodiment. Generally, the syringe-based transfer device 100 (also referred to herein as "bodily-fluid transfer device," "fluid transfer device," or "transfer device") is configured to permit the withdrawal of bodily-fluid from a patient such that a first portion or amount of the withdrawn fluid is fluidically isolated and diverted away from a second portion or amount of the withdrawn fluid that is to be used as a biological sample, such as for testing for the purpose of medical diagnosis and/or treatment. In other words, the transfer device 100 is configured to transfer a first, predetermined amount of a bodily-fluid to a first collection reservoir and a second amount of bodily-fluid to one or more bodily-fluid collection reservoirs (e.g., sample reservoirs) fluidically isolated from the first collection reservoir, as described in more detail herein.

The transfer device 100 includes a housing 101, an actuator mechanism 140, a first fluid reservoir 180 (also referred to herein as "first reservoir" or "pre-sample reservoir"), and a second fluid reservoir 190 (also referred to herein as "second reservoir" or "sample reservoir"), different from the first reservoir 180. The housing 101 can be any suitable shape, size, or configuration and is described in further detail herein with respect to specific embodiments. As shown in FIG. 1, the housing 101 includes a port 105 that can be at least temporarily physically and fluidically coupled to a medical device defining a pathway P for withdrawing and/or conveying the bodily-fluid from the patient to the transfer device 100. For example, the port 105 can be a Luer-Lok® or the like configured to be physically and fluidically coupled to a needle, a cannula, or other lumen-containing device. In other embodiments, the port 105 can be monolithically formed with at least a portion of the lumen-containing device. In this manner, the port 105 can receive the bodily-fluid from the patient via the pathway P as further described herein.

As shown in FIG. 1, the housing 101 defines an inner volume 111 that is configured to receive a portion of the actuator mechanism 140. More specifically, the actuator mechanism 140 is at least partially disposed within the inner volume 111 of the housing 101 and is movable between a first configuration and a second configuration relative to the housing 101. The housing 101 is also configured to house at least a portion of the first reservoir 180 and at least a portion of the second reservoir 190. For example, in some embodiments, the first reservoir 180 and/or the second reservoir 190 can be at least temporarily disposed within the inner volume 111 defined by the housing 101. In other embodiments, the first reservoir 180 and/or the second reservoir 190 can be at least partially defined by a set of walls of the housing 101 that define the inner volume 111. Similarly stated, a portion of the inner volume 111 can form at least a portion of the first reservoir 180 and/or a portion of the second reservoir 190.

The actuator mechanism 140 can be any suitable shape, size, or configuration. For example, in some embodiments, the shape and size of at least a portion of the actuator mechanism 140 substantially corresponds to the shape and size of the walls of the housing 101 defining the inner volume 111. As described above, at least a portion of the actuator mechanism 140 is movably disposed within the inner volume 111 of the housing 101. For example, in some embodiments, a distal end portion of the actuator mechanism 140 is disposed within the inner volume 111 of the housing 101 and a proximal end portion of the actuator mechanism 140 is disposed substantially outside the housing 101. In this manner, a user can engage the proximal end portion of the actuator mechanism 140 to move the portion of the actuator mechanism 140 disposed within the inner volume 111 between the first configuration and the second configuration relative to the housing 101. In some embodiments, the actuator mechanism 140 can be disposed in a third configuration (or storage configuration) relative to the housing 101, as further described herein.

While not shown in FIG. 1, in some embodiments, the actuator mechanism 140 can include a first member and a second member. In such embodiments, both the first member and the second member can be collectively moved within the inner volume 111 of the housing 101. In addition, the first member and the second member can be configured to move independently within the housing 101. Similarly stated, the first member can be moved relative to the second member and/or the second member can be moved relative the first member, as further described below with respect to specific embodiments. In some embodiments, the first member and/or the second member can form a piston or plunger configured to move within the inner volume 111.

Furthermore, a portion of the piston or plunger can form a substantially fluid tight seal with the walls of the housing 101 defining the inner volume 111. In this manner, the housing 101 and the actuator mechanism 140 can collectively form a sealed, air-tight cavity (e.g., a syringe) such that the actuator mechanism 140 (or at least a portion of the actuator mechanism 140) can be configured to introduce or otherwise facilitate the development of a vacuum within the inner volume 111.

The first reservoir 180 can be any suitable reservoir for containing the bodily-fluid. For example, in some embodiments, the first reservoir 180 is defined by a portion of the walls of the housing 101 defining the inner volume 111 and a portion of the actuator mechanism 140. In other embodiments, the first reservoir 180 is defined by only the actuator mechanism 140. In still other embodiments, the first reservoir 180 can be a pre-sample reservoir described in detail in U.S. Pat. No. 8,197,420 ("the '420 patent"), the disclosure of which is incorporated herein by reference in its entirety. In this manner, the first reservoir 180 can be selectively placed in fluid communication with the housing 101 or the actuator mechanism 140 either directly (e.g., physically and fluidically coupled to the housing 101 or the actuator mechanism 140) or indirectly (e.g., fluidically coupled via intervening structure such as sterile flexible tubing).

The first reservoir 180 is configured to receive and contain the first, predetermined amount of the bodily-fluid. More specifically, when the actuator mechanism 140 is in the first configuration, a portion of the actuator mechanism 140 and a portion of the housing 101 can define a first fluid flow path 181 configured to fluidically couple the port 105 of the housing 101 to the first reservoir 180. In some embodiments, the actuator mechanism 140 can be moved to the first configuration (e.g., from the third configuration described above) and can introduce a vacuum that facilitates the flow of the bodily-fluid through the first flow path 181 and into the first reservoir 180. The first reservoir 180 is configured to contain the first amount of the bodily-fluid such that the first amount is fluidically isolated from a second amount of the bodily-fluid (different than the first amount of bodily-fluid) that is subsequently withdrawn from the patient.

The second reservoir 190 can be any suitable reservoir and is configured to receive and contain the second amount of the bodily-fluid. In some embodiments, the second reservoir 190 is defined by a portion of the walls of the housing 101 defining the inner volume 111 and a portion of the actuator member 140. In this manner, when the actuator mechanism 140 is in the second configuration, a portion of the actuator mechanism 140 and a portion of the housing 101 can define a second fluid flow path 191 configured to fluidically couple the port 105 to the second reservoir 190. In some embodiments, the movement of the actuator mechanism 140 to the second configuration can be such that a second vacuum force facilitates the flow of the bodily-fluid through the second flow path 191 and into the second reservoir 190. The second amount of bodily-fluid can be an amount withdrawn from the patient subsequent to withdrawal of the first amount. In some embodiments, the second reservoir 190 is configured to contain the second amount of the bodily-fluid such that the second amount is fluidically isolated from the first amount of the bodily-fluid.

As described above, the transfer device 100 can be used to transfer a bodily-fluid from a patient to the first reservoir 180 and/or second reservoir 190 included in the transfer device 100. More specifically, the flow of the first amount of bodily-fluid transferred to the first reservoir 180 can be such that dermally-residing microbes dislodged during a venipuncture event and/or other external sources (e.g. ambient airborne microbes, transferred from the skin of the practitioner collecting the sample, etc.) become entrained in the flow and are thereby transferred to the first reservoir 180. In addition, the first reservoir 180 fluidically isolates the first amount such that when the subsequent second amount is withdrawn into the second reservoir 190, the second amount is substantially free from the dermally-residing microbes. Although not shown in FIG. 1, in some embodiments, the syringe-based transfer device 100 can be coupled to a device in fluid communication with the patient that is also configured to reduce contamination of a patient sample. For example, in some embodiments, the syringe-based transfer device 100 can be used with a lumenless needle or the like such as those described in U.S. Patent Application Ser. No. 61/777,758, entitled "Lumenless Needle for Bodily-Fluid Sample Collection," filed on Mar. 12, 2013 ("the '758 application") the disclosure of which is incorporated herein by reference in its entirety.

In some embodiments, the transfer device 100 can be configured such that the first amount of bodily-fluid need be conveyed to the first reservoir 180 before the transfer device 100 will permit the flow of the second amount of bodily-fluid to be conveyed through the second flow path 191 to the second reservoir 180. In this manner, the transfer device 100 can be characterized as requiring compliance by a health care practitioner regarding the collection of the first, predetermined amount (e.g., a pre-sample) prior to collection of the second amount (e.g., a sample) of bodily-fluid. Similarly stated, the transfer device 100 can be configured to prevent a health care practitioner from collecting the second amount, or the sample, of bodily-fluid into the second reservoir 190 without first diverting the first amount, or pre-sample, of bodily-fluid into the first reservoir 180. In this manner, the health care practitioner is prevented from including (whether intentionally or unintentionally) the first amount of bodily-fluid, which is more likely to contain dermally-residing microbes and/or other external undesirable contaminants, in the bodily-fluid sample to be used for analysis. In other embodiments, the fluid transfer device 100 need not include a forced-compliance feature or component.

In some embodiments, the actuator mechanism 140 can have a fourth configuration, different than the first, second, and third configurations. In such embodiments, the actuator mechanism 140 can be moved towards the fourth configuration when the transfer device 100 has collected the second amount of the bodily-fluid and has been removed from contact with the patient. When in the fourth configuration, the first fluid reservoir 180 can maintain the first amount of bodily-fluid in fluid isolation and the second fluid reservoir 190 can be maintained in fluid communication with the port 105. Therefore, when the actuator mechanism 140 is moved toward the fourth configuration the transfer device 100 can transfer a portion of the second amount of the bodily-fluid from the second reservoir 190 to any suitable container (e.g., a vile, a test tube, a petri dish, a culture medium, a test apparatus, or the like) such that the portion of the second amount of bodily-fluid can be tested.

FIGS. 2-6 illustrate a syringe-based transfer device 200 according to an embodiment. The syringe-based transfer device 200 (also referred to herein as "bodily-fluid transfer device," "fluid transfer device," or "transfer device") includes a housing 201 and an actuator mechanism 240. Furthermore, the transfer device 200 is configured to include or define a first fluid reservoir 280 (also referred to herein as "first reservoir" or "pre-sample reservoir") and a second fluid reservoir 290 (also referred to herein as "second reservoir" or "sample reservoir"). The transfer device 200 can be any suitable shape, size, or configuration. For example, while shown in FIGS. 2 and 3 as being substantially cylindrical, the transfer device 200 can be square, rectangular, polygonal, and/or any other non-cylindrical shape.

Figure 2:
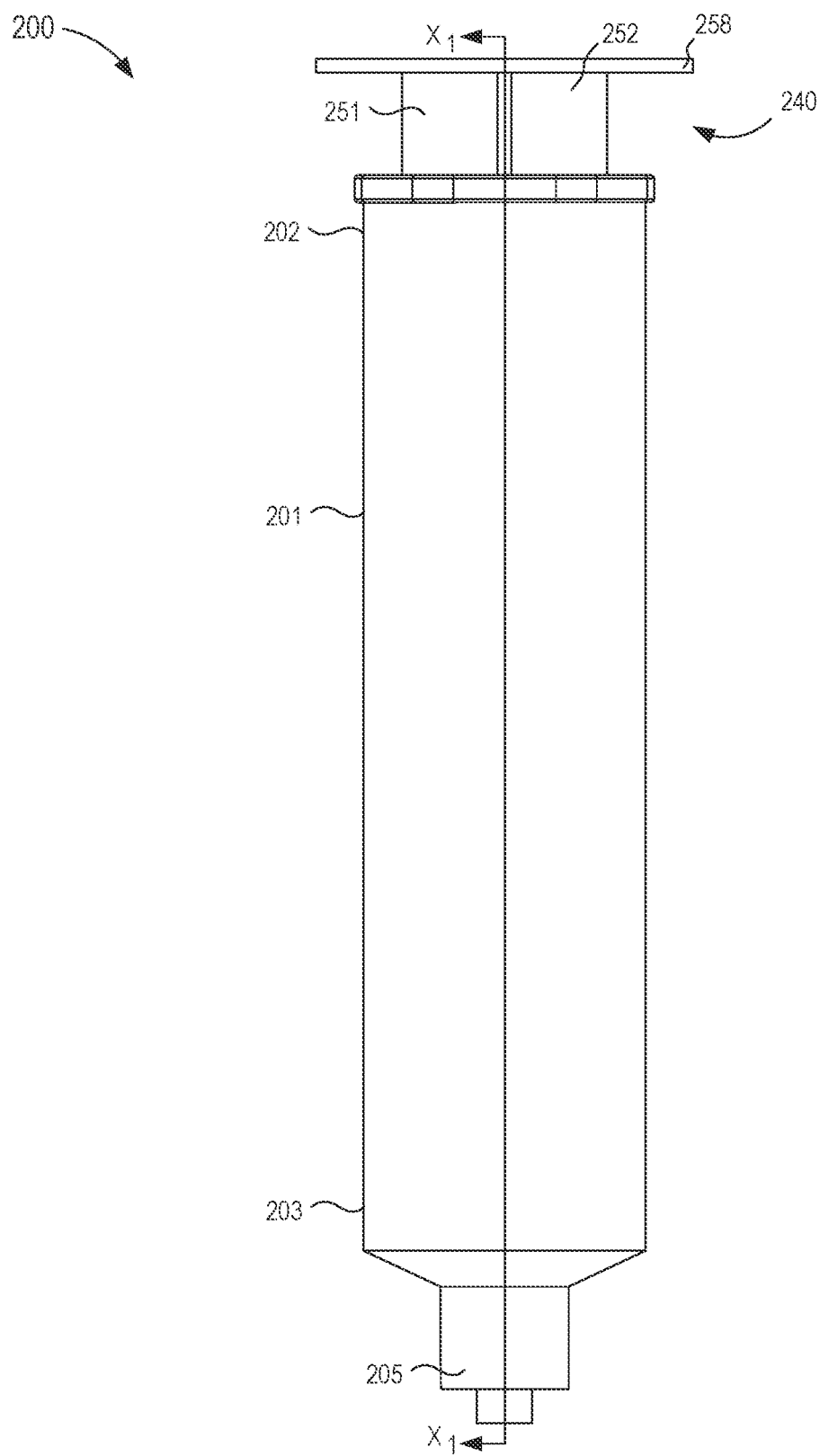
FIG. 2 is a front view of a syringe-based transfer device according to an embodiment, in a first configuration.
Figure 3:
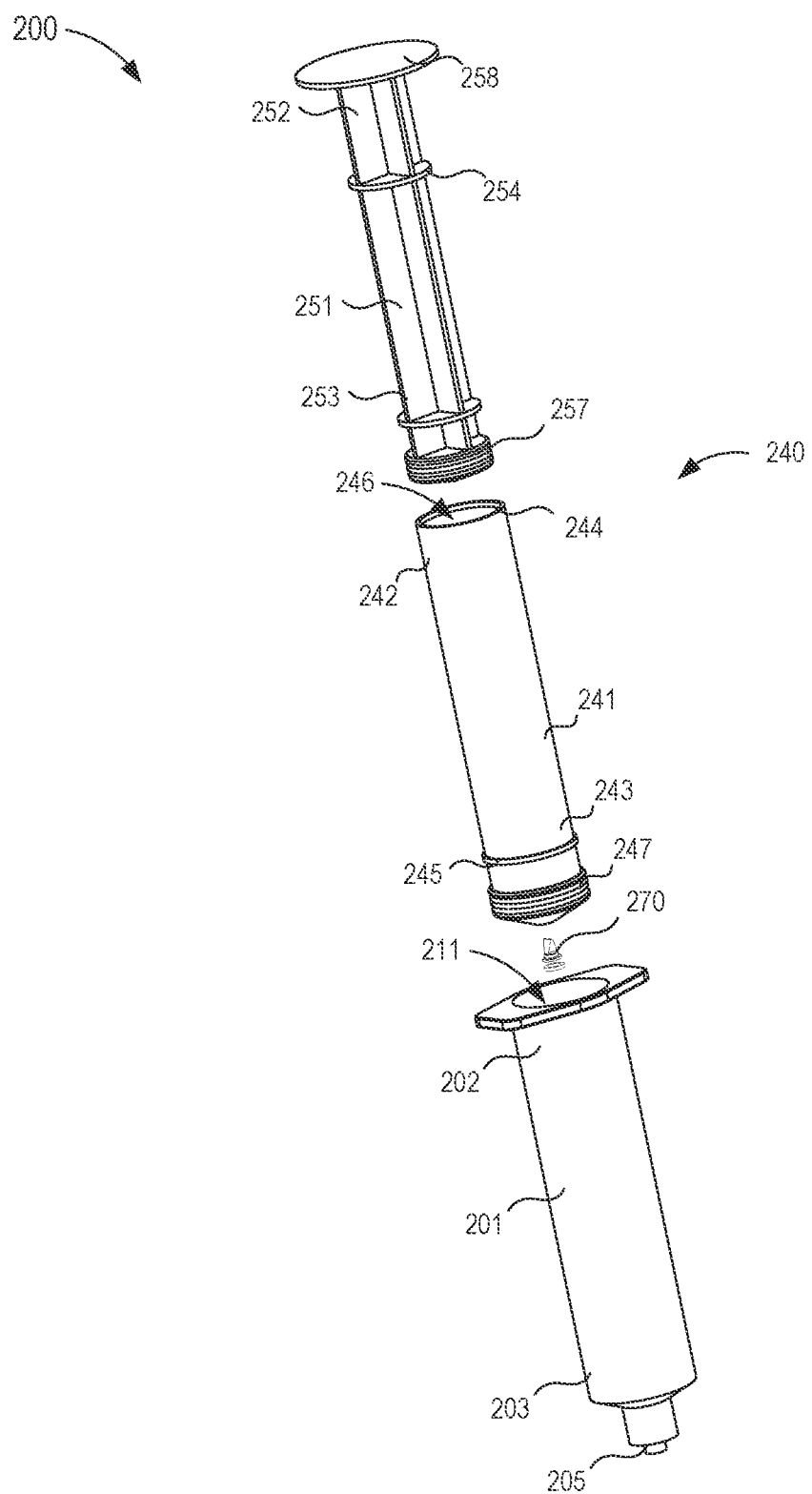
FIG. 3 is an exploded view of the syringe-based transfer device of FIG. 2.
Figure 4:
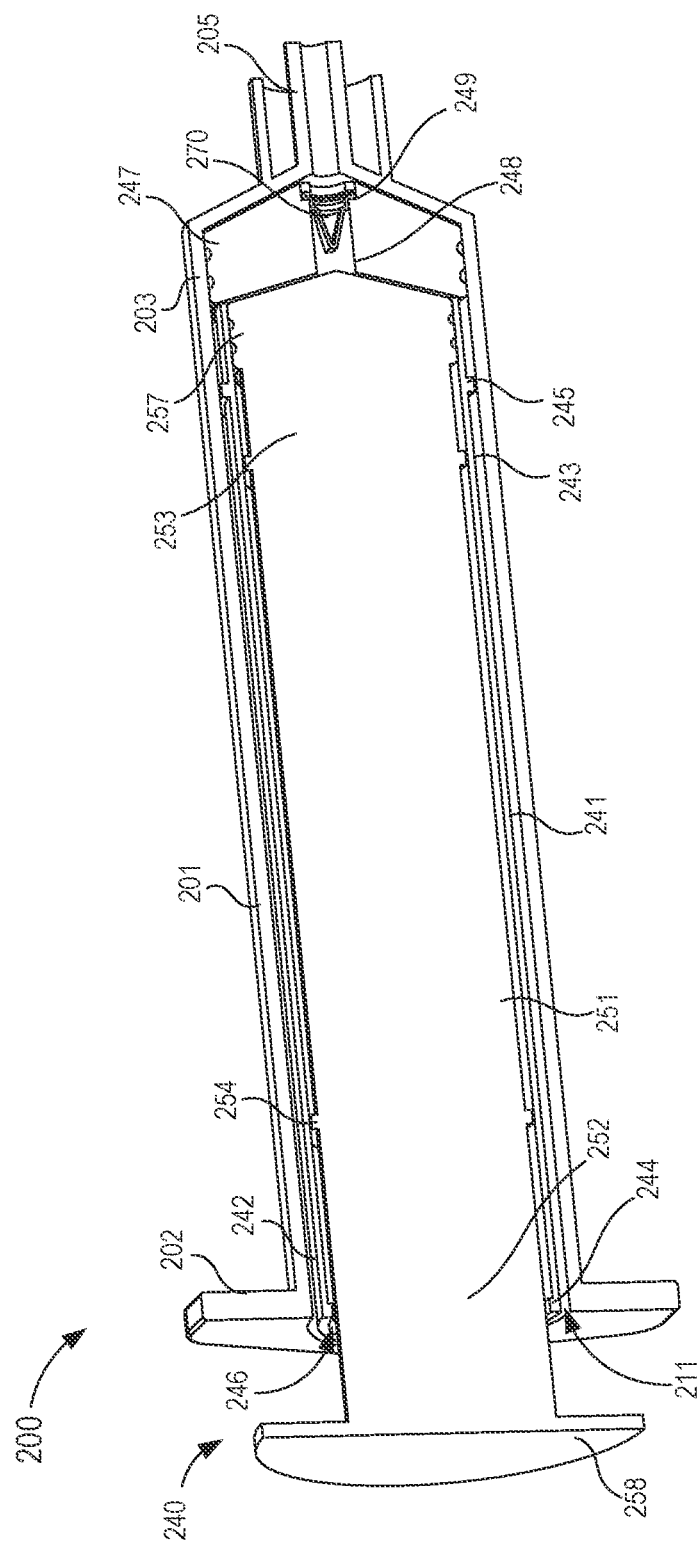
FIG. 4 is a cross-sectional view of the syringe-based transfer device illustrated in FIG. 2 taken along the line $X_1$-$X_1$, in the first configuration.

As shown in FIGS. 2 and 3, the housing 201 includes a proximal end portion 202 and a distal end portion 203 and defines an inner volume 211 therebetween. In some embodiments, the housing 201 can be substantially similar to a syringe body. The proximal end portion 202 of the housing 201 is substantially open and is configured to receive at least a portion of the actuator mechanism 240 such that the portion of the actuator mechanism 240 is movably disposed within the inner volume 211. Furthermore, the inner volume 211 is configured to define the second fluid reservoir 290, as further described herein. The distal end portion 203 of the housing 201 includes a port 205. In some embodiments, the port 205 can be monolithically formed with the housing 201 (e.g., as shown in FIGS. 2-6). In other embodiments, the port 205 can be coupled to the distal end portion 203 in any suitable manner such as, for example, via a friction fit, a threaded coupling, a mechanical fastener, an adhesive, any number of mating recesses, and/or any combination thereof.

The port 205 can be any suitable shape, size, or configuration. For example, in some embodiments, at least a portion of the port 205 can form a lock mechanism configured to be physically and fluidically coupled to a needle, a cannula, or other lumen-containing device. For example, in some embodiments, the port 205 can be a Luer-Lok® or similar locking mechanism configured to physically and fluidically couple to a needle or cannula assembly (not shown in FIGS. 2-6). In other embodiments, the port 205 can be monolithically formed with at least a portion of the lumen-containing device. In this manner, the port 205 can be placed in fluid communication with a lumen defined by the lumen-defining device and to receive the bodily-fluid from a patient when the lumen-defining device is disposed within the patient (e.g., as a result of a venipuncture event), as further described herein.

As described above, the actuator mechanism 240 is disposed within the inner volume 211 and is movable between a first position (e.g., a distal position relative to the housing 201) and a second position (e.g., a proximal position relative to the housing 201). Furthermore, the movement of the actuator mechanism 240 relative to the housing 201 can move the transfer device 200 between a first, second, and third configuration, as further described herein. The actuator mechanism 240 includes a first member 241 and a second member 251. The first member 241 of the actuator mechanism 240 includes a proximal end portion 242 and a distal end portion 243 and defines an inner volume 246 therebetween. At least a portion of the inner volume 246 is configured to define the first reservoir 280, as further described herein.

The proximal end portion 242 is substantially open such that at least a portion of the second member 251 can be movably disposed within the inner volume 246. The proximal end portion 242 also includes a protrusion 244 that extends from an inner surface of a wall (or set of walls) defining the inner volume 246 and is configured to selectively engage a portion of the second member 251.

The distal end portion 243 of the first member 241 includes a plunger 247. The plunger 247 is configured to form a friction fit with the inner surface of the walls defining the inner volume 211 when the actuator mechanism 240 is disposed within the housing 201. Similarly stated, the plunger 247 defines a fluidic seal with the inner surface of the walls defining the inner volume 211 such that a portion of the inner volume 211 proximal of the plunger 247 is fluidically isolated from a portion of the inner volume 211 distal of the plunger 247. The plunger 247 is further configured to define a channel 248 that extends though a distal end and a proximal end of the plunger 247. Moreover, a portion of an inner set of walls defining the channel 248 is configured to form a valve seat 249. In this manner, a portion of the channel 248 can receive a valve 270 that is in contact with the valve seat 249.

The valve 270 can be any suitable valve. For example, in some embodiments, the valve 270 is a one-way check valve configured to allow a flow of a fluid from a distal end of the valve 270 to a proximal end of the valve 270 but substantially not allow a flow of the fluid from the proximal end to the distal end. In addition, the valve 270 can be disposed within the channel 248 and can be in contact with the valve seat 249 such that the valve 270 forms a substantially fluid tight seal with the walls defining the channel 248. In some embodiments, the valve 270 can form a first fit with walls defining the channel 248. In other embodiments, the valve 270 can form a threaded coupling or the like with at least a portion of the walls. The valve 270 can also include a seal member configured to engage the valve seat 249 thereby forming at least a portion of the fluid tight seal. The arrangement of the plunger 247 and the valve 270 is such that when the valve 270 is in the open configuration, the inner volume 246 defined by the first member 241 is placed in fluid communication with the portion of the inner volume 211 of the housing 201 that is distal of the plunger 247, as further described herein.

The second member 251 of the actuator mechanism 240 includes a proximal end portion 252 and a distal end portion 253. The proximal end portion 252 includes an engagement portion 258 that can be engaged by a user (e.g., a phlebotomist, a nurse, a technician, a physician, etc.) to move at least a portion of the actuator mechanism 240 relative to the housing 201. The distal end portion 253 includes a plunger 257 configured to form a friction fit with the inner surface of the walls defining the inner volume 246 when the second member 251 is disposed with the first member 241. Similarly stated, the plunger 257 defines a fluidic seal with the inner surface of the walls defining the inner volume 246 such that a portion of the inner volume 246 proximal of the plunger 257 is fluidically isolated from a portion of the inner volume 246 distal of the plunger 257.

As described above, at least a portion the second member 251 is configured to be movably disposed within the inner volume 246 of the first member 241. More specifically, the second member 251 can be movable between a first position (e.g., a distal position) and a second position (e.g., a proximal position) thereby moving the actuator mechanism 240 between a first configuration and a second configuration, respectively. In addition, the second member 251 includes a protrusion 254 that extends in a radial direction to selectively engage the protrusion 244 of the first member 241. In this manner, the protrusion 244 of the first member 241 and the protrusion 254 of the second member 251 can be placed in contact to substantially limit a proximal movement of the second member 251 relative the first member 241.

In use, a user can engage the transfer device 200 to couple the port 205 to a proximal end portion of a lumen-defining device (not shown) such as, for example, a butterfly needle, a cannula assembly, a trocar (which is some cases is used to insert a catheter into a patient), or the like. With the port 205 physically coupled to the lumen-defining device, the port 205 is placed in fluid communication with the lumen defined by the lumen-defining device. Furthermore, the distal end portion of the lumen-defining device can be disposed within a portion of the body of a patient (e.g., a vein). In this manner, the port 205 is placed in fluid communication with the portion of the body.

With the port 205 coupled to the lumen-defining device, a user (e.g., a phlebotomist, a nurse, a technician, a physician, or the like) can move the transfer device 200 from the first configuration to the second configuration. More specifically, the user can engage the engagement portion 258 of the second member 251 included in the actuator mechanism 240 to move the actuator mechanism 240 from its first configuration to its second configuration, thereby placing the transfer device 200 in the second configuration, as indicated by the arrow AA in FIG. 5. In this manner, the second member 251 of the actuator mechanism 240 is moved in a proximal direction relative to the first member 241 (e.g., the first member 241 does not substantially move in the proximal direction) until the protrusion 254 of the second member 251 is placed into contact with the protrusion 244 of the first member 241.

The arrangement of the second member 251 within the first member 241 is such that the proximal motion of the second member 251 increases the volume of the portion of the inner volume 246 that is distal of the plunger 257, thereby defining the first reservoir 280. Furthermore, with the plunger 257 forming a fluid tight seal with the inner surface of the walls defining the inner volume 246, the increase of volume can produce a negative pressure within the first reservoir 280.

Figure 5:
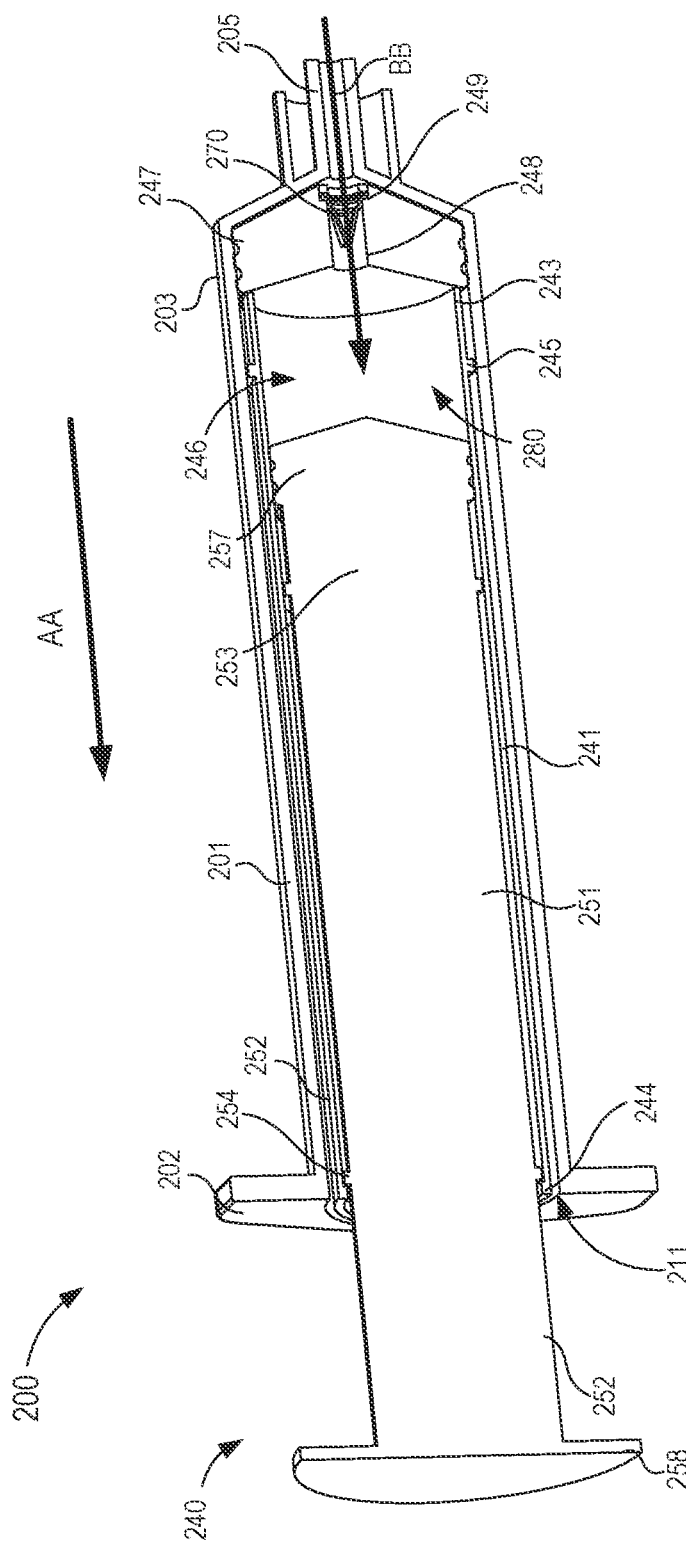
FIG. 5 is a cross-sectional view of the syringe-based transfer device of FIG. 2 taken along the line $X_1$-$X_1$, in a second configuration.

As shown by the arrow BB in FIG. 5, the port 205, the valve 270, and the channel 248 define a fluid flow path that places the first reservoir 280 in fluid communication with the lumen-defining device. Therefore, the first reservoir 280 is placed in fluid communication with the portion of the patient (e.g., the vein). Expanding further, the negative pressure within the first reservoir 280 can be operative in moving the valve 270 from a closed configuration to an open configuration. In this manner, the negative pressure within the first reservoir 280 produced by the movement of the plunger 257 introduces a suction force within the portion of the patient. Thus, a bodily-fluid is drawn through the port 205 and the valve 270 and into the first reservoir 280. In some embodiments, the bodily-fluid can contain undesirable microbes such as, for example, dermally-residing microbes and/or other external contaminants.

In some embodiments, the magnitude of the suction force can be modulated by increasing or decreasing the amount of a force applied to the actuation mechanism 240. For example, in some embodiments, it can be desirable to limit the amount of suction force introduced to a vein. In such embodiments, the user can reduce the amount of force applied to the engagement portion 258 of the second member 251. In this manner, the rate of change (e.g., the increase) in the volume of the first reservoir 280 can be sufficiently slow to allow time for the negative pressure differential between the vein and the fluid reservoir to come to equilibrium before further increasing the volume of the first reservoir 280. Thus, the magnitude of the suction force can be modulated.

While in the second configuration, the transfer device 200 can be configured to transfer a desired amount (e.g., a predetermined amount) of bodily-fluid transferred to the first reservoir 280. In some embodiments, the first, predetermined amount can substantially correspond to the size of the first reservoir 280. In other embodiments, the first amount can substantially correspond to an equalization of pressure within the first reservoir 280 and the portion of the patient. Moreover, in such embodiments, the equalization of the pressure can be such that the valve 270 is allowed to return to the closed configuration. Thus, the first reservoir 280 is fluidically isolated from a volume substantially outside the first reservoir 280.

With the first amount fluidically isolated, the actuator mechanism 240 can be moved from the second configuration to a third configuration by further moving the actuator mechanism 240 in the proximal direction. For example, as indicated by the arrow CC in FIG. 6, the user can apply a force to the engagement portion 258 of the second member 251 to move the actuator mechanism 240 relative to the housing 201. Expanding further, with the protrusion 254 of the second member 251 in contact with the protrusion 244 of the first member 241, the further application of force on the engagement portion 258 is such that the first member 241 and the second member 251 collectively move in the proximal direction relative to the housing 201.

The arrangement of the first member 241 within the inner volume 211 of the housing 201 is such that the proximal motion of the first member 241 increases the volume of the portion of the inner volume 211 that is distal of the plunger 247, thereby defining the second reservoir 290. Furthermore, with the plunger 247 forming a fluid tight seal with the inner surface of the walls defining the inner volume 211 and with the valve 270 in the closed configuration, the increase of volume can produce a negative pressure within the second reservoir 290.

Figure 6:
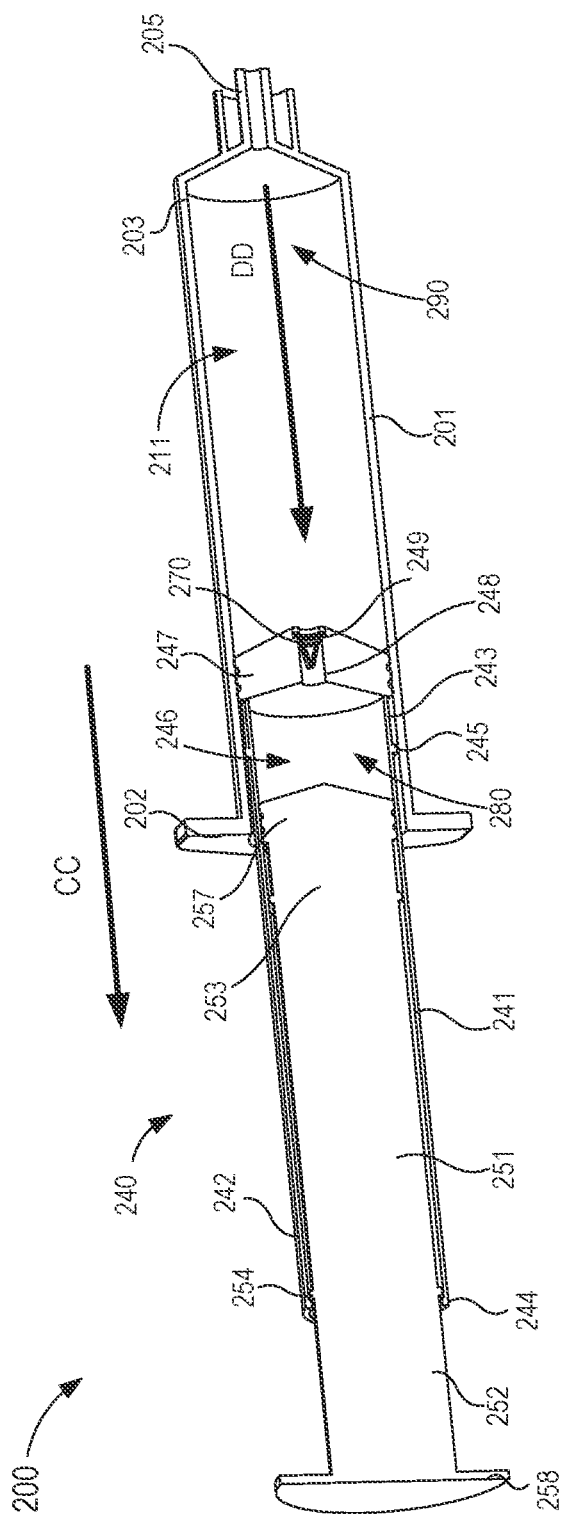
FIG. 6 is a cross-sectional view of the syringe-based transfer device of FIG. 2 taken along the line $X_1$-$X_1$, in a third configuration.

As shown by the arrow DD in FIG. 6, the port 205 and a portion of the inner volume 211 define a fluid flow path that places the second reservoir 290 in fluid communication with the lumen-defining device. Therefore, the second reservoir 290 is placed in fluid communication with the portion of the patient (e.g., the vein). Expanding further, the negative pressure within the second reservoir 290 produced by the movement of the plunger 247 introduces a suction force within the portion of the patient. Thus, a bodily-fluid is drawn through the port 205 and into the second reservoir 290. In addition, the bodily-fluid contained within the second reservoir 290 is substantially free from microbes generally found outside of the portion of the patient (e.g., dermally residing microbes, microbes within a lumen defined by the transfer device 200, microbes within the lumen defined by the lumen defining device, and/or any other undesirable microbe).

While not shown in FIGS. 2-6, the actuator mechanism 240 can be moved from the third configuration to a fourth configuration to place the transfer device 200 in a fourth configuration. For example, in some embodiments, with the desired amount of bodily-fluid disposed within the second fluid reservoir 290, the transfer device 200 can be removed from the portion of the patient and disposed above or in a container (e.g., a vile, a test tube, a petri dish, a culture medium, a test apparatus, a cartridge designed for use with an automated, rapid microbial detection system, or the like) such that at least a portion of the second amount of bodily-fluid can be tested. The withdrawn bodily-fluid can be used for any number of testing processes or procedures such as, for example, blood culture testing, real-time diagnostics, and/or PCR-based approaches. Expanding further, the user can apply a force to the engagement portion 258 of the second member 251 to move the actuator mechanism 240 in the distal direction (e.g., opposite the arrow CC shown in FIG. 6). With the valve 270 in the closed configuration the bodily-fluid contained within the first reservoir 280 is maintained in fluid isolation with a volume outside the first reservoir 280. In some embodiments, the volume of the first reservoir 280 is sufficient to contain the first centiliter or few centiliters of bodily-fluid. In other embodiments, the first reservoir 280 can be configured to contain from about 0.1 ml to about 3.0 ml. In still other embodiments, the first reservoir 280 can be configured to contain from about 3.0 ml, 4.0 ml, 5.0 ml, 6.0 ml, 7.0 ml, 8.0 ml, 9.0 ml, 10.0 ml, 15.0 ml, 20.0 ml, 25.0 ml, 50 ml, or any volume or fraction of volume therebetween. Furthermore, the pressure within the first reservoir 280 can be such that the force applied to the second member 251 does not substantially move the second member 251 relative to the first member 241. Thus, the force applied to the engagement portion 258 collectively moves the second member 251 and the first member 241 in the distal direction relative to the housing 201 to expel a desired portion of the second amount of bodily-fluid from the lumen-defining device and into the container.

Although not shown in FIGS. 2-6, in some embodiments, the syringe-based transfer device 200 can be coupled to a device in fluid communication with the patient that is also configured to reduce contamination of a patient sample. For example, in some embodiments, the syringe-based transfer device 200 can be used with a lumenless needle or the like such as those described in the '758 application.

FIGS. 7-10 illustrate a syringe-based transfer device 300 according to an embodiment. The syringe-based transfer device 300 (also referred to herein as "bodily-fluid transfer device," "fluid transfer device," or "transfer device") is configured to be moved between a first, second, third, and fourth configuration, as further described herein. The transfer device 300 includes a housing 301 and an actuator 341. Furthermore, the transfer device 300 is configured to include or define a first fluid reservoir 380 (also referred to herein as "first reservoir" or "pre-sample reservoir") and a second fluid reservoir 390 (also referred to herein as "second reservoir" or "sample reservoir"). The transfer device 300 can be any suitable shape, size, or configuration. For example, while shown in FIGS. 7 and 8 as being substantially cylindrical, the transfer device 300 can be square, rectangular, polygonal, and/or any other non-cylindrical shape. Moreover, portions of the transfer device 300 can be substantially similar to the corresponding portions of the transfer device 200, described above in reference to FIGS. 2-6. Therefore, such portions are not described in further detail herein and should be considered substantially similar unless explicitly described differently.

Figure 7:
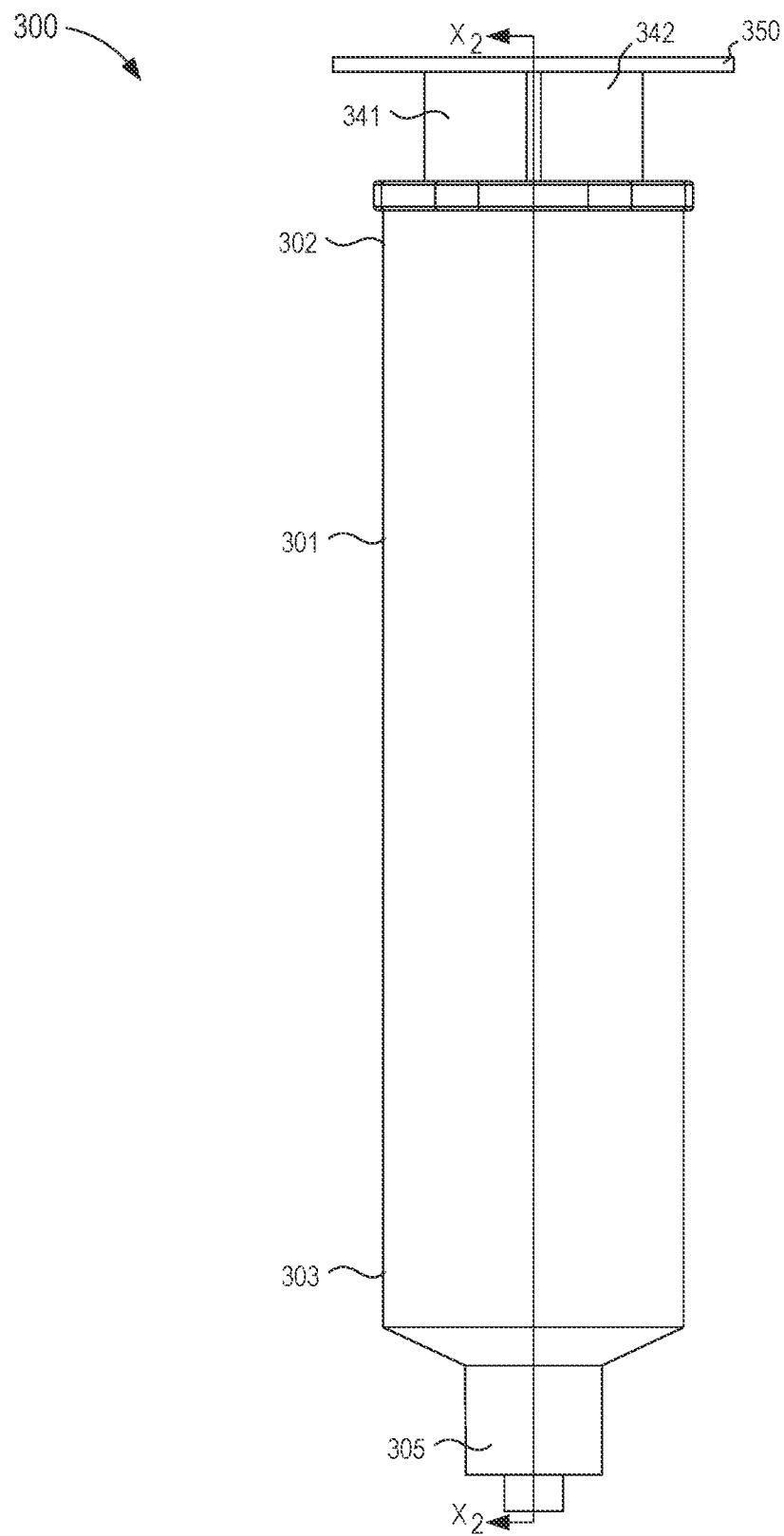
FIG. 7 is a front view of a syringe-based transfer device according to an embodiment, in a first configuration.
Figure 8:
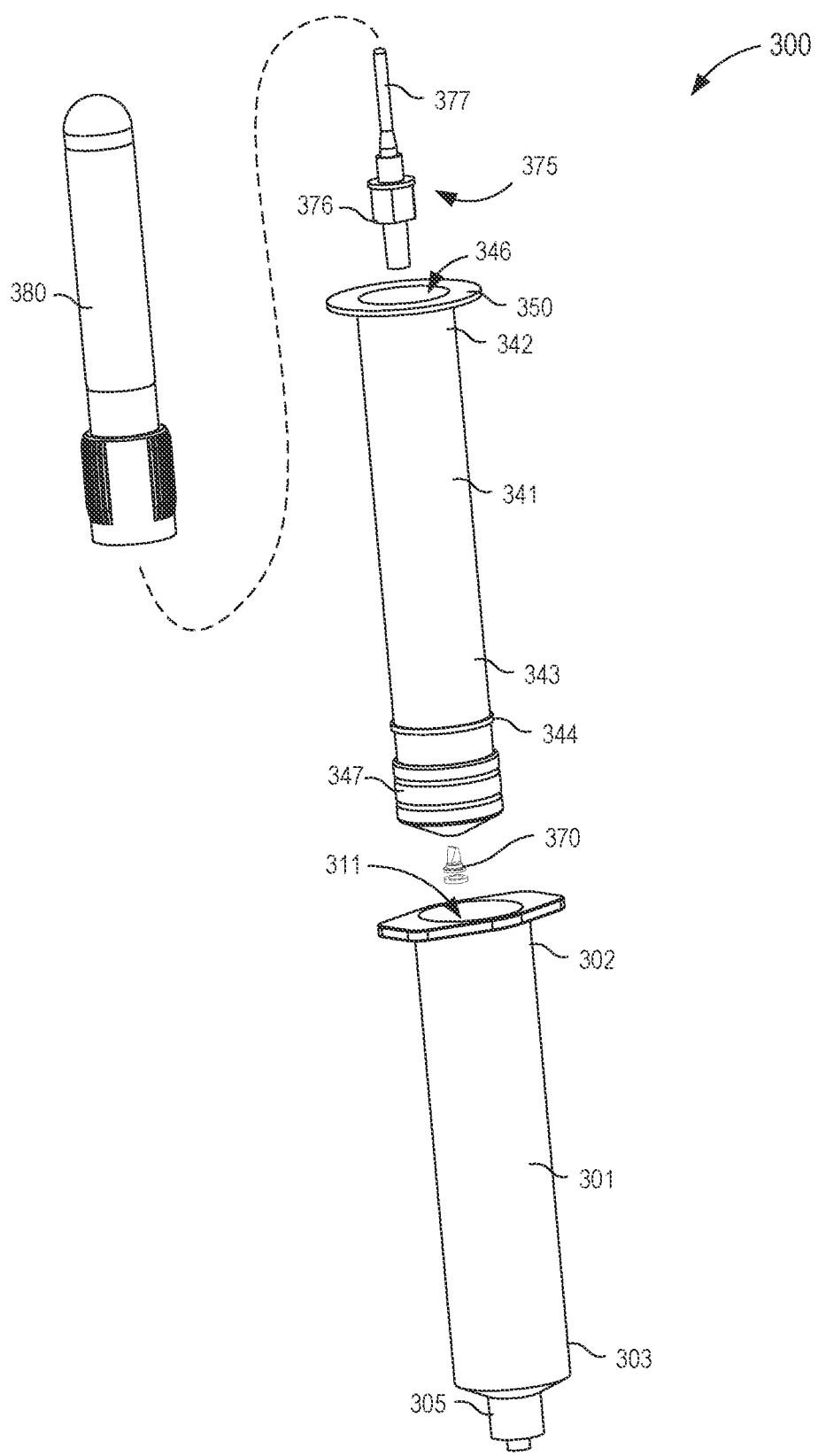
FIG. 8 is an exploded view of the syringe-based transfer device of FIG. 7.

As shown in FIGS. 7 and 8, the housing 301 includes a proximal end portion 302 and a distal end portion 303 and defines an inner volume 311 therebetween. The proximal end portion 302 of the housing 301 is substantially open and is configured to receive at least a portion of the actuator 341 such that the portion of the actuator 341 is movably disposed within the inner volume 311. Furthermore, the inner volume 311 is configured to define the second fluid reservoir 390, as further described herein. The distal end portion 303 of the housing 301 includes a port 305. The port 305 is configured to be coupled to or monolithically formed with a lumen-containing device, such as those described above.

As described above, the actuator 341 is disposed within the inner volume 311 and is movable between a first position (e.g., a distal position relative to the housing 301) and a second position (e.g., a proximal position relative to the housing 301). The actuator 341 includes a proximal end portion 342 and a distal end portion 343 and defines an inner volume 346 therebetween. The proximal end portion 342 includes an engagement portion 350, as described above with respect to the second member 251 of the actuator mechanism 240. In addition, the proximal end 342 is substantially open such that at least a portion of the first reservoir 380 can be movably disposed within the inner volume 346.

The distal end portion 343 of the actuator 341 includes a plunger 347. The plunger 347 is configured to form a friction fit with the inner surface of the walls defining the inner volume 311 when the actuator 341 is disposed within the housing 301, as described in detail above in reference FIGS. 2-6. The plunger 347 also defines a channel 348 that extends though a distal end and a proximal end of the plunger 347. The channel 348 is configured to receive a port 375 having a base 376 and a piercing member 377. The base 376 can be disposed within the channel 348 and forms a friction fit with a set walls defining the channel 348. In this manner, the base 376 and the walls defining the channel 348 can form a substantially fluid tight seal. The piercing member 377 of the port 375 is configured to extend in the proximal direction from the base 376. As shown in FIG. 8, the piercing member 377 can be disposed within a sheath configured to be selectively moved to expose, for example, a needle. For simplicity, FIGS. 8-10 only illustrate a sheath of the piercing member and not the needle disposed therein.

A portion of the set of walls defining the channel 348 is configured to form a valve seat 349. In this manner, a portion of the channel 348 can receive a valve 370 such that the valve 370 is in contact with the valve seat 349. The valve 370 can be any suitable configuration, for example, the valve 370 can be similar in form and function to the valve 270 described above. In this manner, the arrangement of the plunger 347 and the valve 370 is such that when the valve 370 is in the open configuration, the port 375 is placed in fluid communication with the portion of the inner volume 311 of the housing 301 that is distal of the plunger 347, as further described herein.

In use, a user can engage the transfer device 300 to couple the port 305 to a proximal end portion of a lumen-defining device (not shown) such as, for example, a butterfly needle, a cannula assembly, a trocar (which in some cases is used to insert a catheter into a patient), or the like. With the port 305 physically coupled to the lumen-defining device, the port 305 is placed in fluid communication with the lumen defined by the lumen-defining device. Furthermore, the distal end portion of the lumen-defining device can be disposed within a portion of the body of a patient (e.g., a vein). In this manner, the port 305 is placed in fluid communication with the portion of the body.

With the port 305 coupled to the lumen-defining device, a user (e.g., a phlebotomist, a nurse, a technician, a physician, or the like) can move the transfer device 300 from the first configuration to the second configuration. In this manner, the user can engage the first reservoir 380 and place the first reservoir 380 within the inner volume 346 defined by the actuator 341. More specifically, as shown in FIG. 8, the first reservoir 380 can be an external fluid reservoir configured to receive a fluid. For example, in some embodiments, the first reservoir 380 can be a Vacutainer® and/or a monolithically formed chamber in the transfer device 300 with or without a negative pressure. In other embodiments, the first reservoir 380 can be a pre-sample reservoir such as those disclosed in the '420 patent. In this manner, the first reservoir 380 can be placed within the inner volume 346 of the actuator 341, as indicated by the arrow EE in FIG. 9.

The insertion of the first reservoir 380 into the inner volume 346 of the actuator 341 can place the transfer device 300 in the second configuration. Furthermore, the distal end portion of the first reservoir 380 can be configured to include a pierceable septum that can receive the piercing member 377 of the port 375. While not shown in FIG. 9, the distal end portion of the first reservoir 380 can engage the port 375 such that the sheath of the piercing member 377 is moved, thereby exposing the needle. Thus, the needle can pierce the septum of the first reservoir 380 to place the first reservoir 380 in fluid communication with the port 375. The arrangement of the first reservoir 380 can also be such that the inner volume defined therein is substantially evacuated. Similarly stated, the inner volume of the first reservoir 380 defines a negative pressure.

Figure 9:
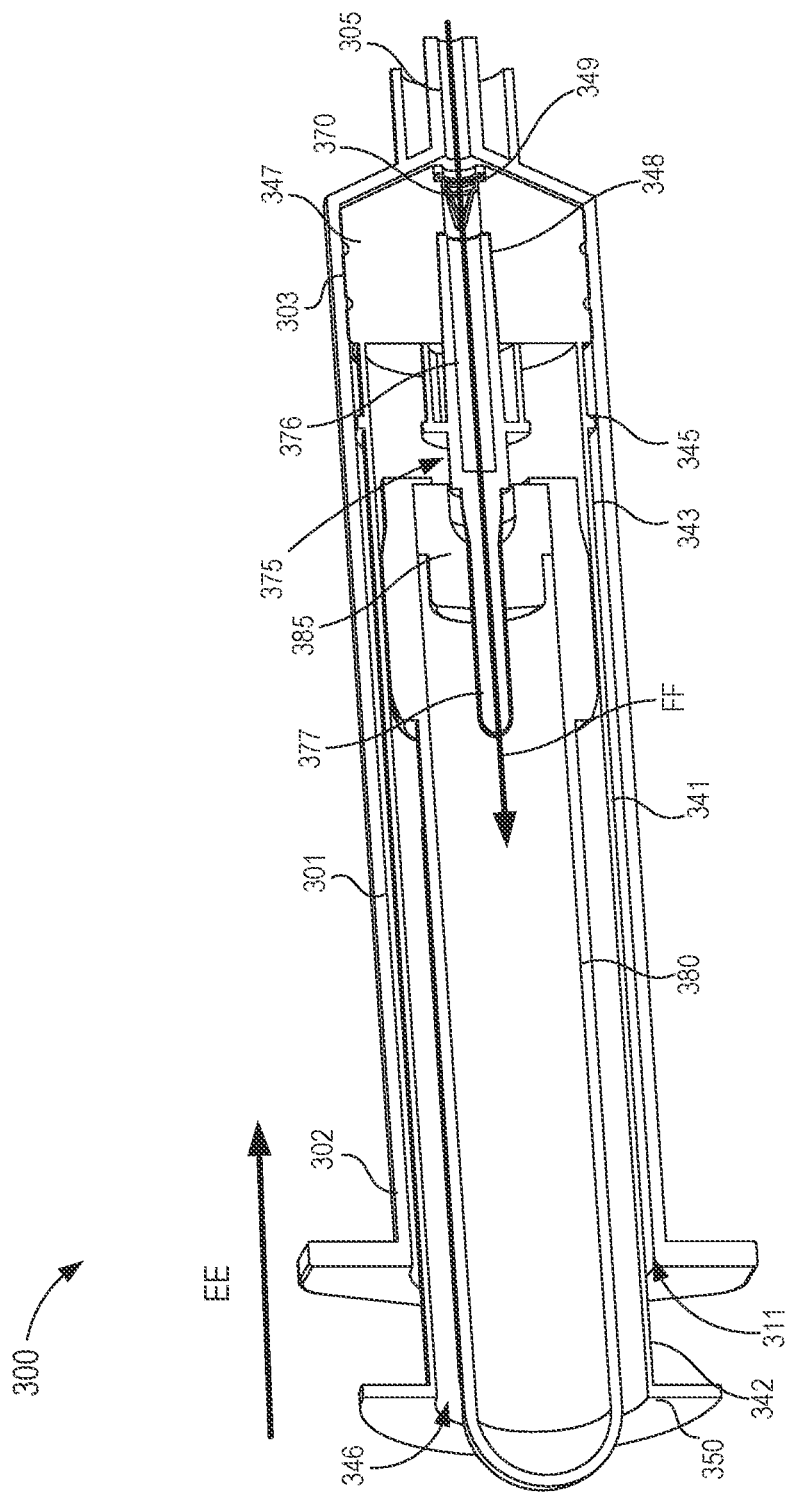
FIG. 9 is a cross-sectional view of the syringe-based transfer device of FIG. 7 taken along the line $X_2 X_2$, in the first configuration.

As shown by the arrow FF in FIG. 9, the port 305, the valve 370, and the port 375 define a fluid flow path such that the first reservoir 380 is in fluid communication with the lumen-defining device. Therefore, the first reservoir 380 is placed in fluid communication with the portion of the patient (e.g., the vein, the spinal cavity, etc.). Expanding further, the negative pressure within the first reservoir 380 can be operative in moving the valve 370 from a closed configuration to an open configuration. In this manner, the negative pressure within the within the first reservoir 380 introduces a suction force within the portion of the patient. Thus, a bodily-fluid is drawn through the port 305, the valve 370, and the port 375 and into the first reservoir 380. In some embodiments, the bodily-fluid can contain undesirable microbes such as, for example, dermally-residing microbes and/or other external contaminants.

While in the second configuration, the transfer device 300 can be configured to transfer a desired amount (e.g., a predetermined amount) of bodily-fluid transferred to the first reservoir 380. In some embodiments, the first, predetermined amount can substantially correspond to an equalization of pressure within the first reservoir 380 and the portion of the patient. Moreover, in such embodiments, the equalization the pressure can be such that the valve 370 is allowed to return to the closed configuration. Thus, the first reservoir 380 is fluidically isolated from a volume substantially outside the first reservoir 380.

With the first amount of bodily-fluid (e.g., the amount containing dermally-residing microbes) fluidically isolated, the first reservoir 380 can be removed from the inner volume 346 of the actuator 341 and discarded. In this manner, the actuator 341 can be moved from the second configuration to a third configuration by moving the actuator 341 in the proximal direction. For example, as indicated by the arrow GG in FIG. 10, the user can apply a force to the engagement portion 350 of the actuator 341 to move the actuator 341 relative to the housing 301. The arrangement of the actuator 341 within the inner volume 311 of the housing 301 is such that the proximal motion of the actuator 341 increases the volume of the portion of the inner volume 311 that is distal of the plunger 347, thereby defining the second reservoir 390. Furthermore, with the plunger 347 forming a fluid tight seal with the inner surface of the walls defining the inner volume 311 and with the valve 370 in the closed configuration, the increase of volume can produce a negative pressure within the second reservoir 390.

Figure 10:
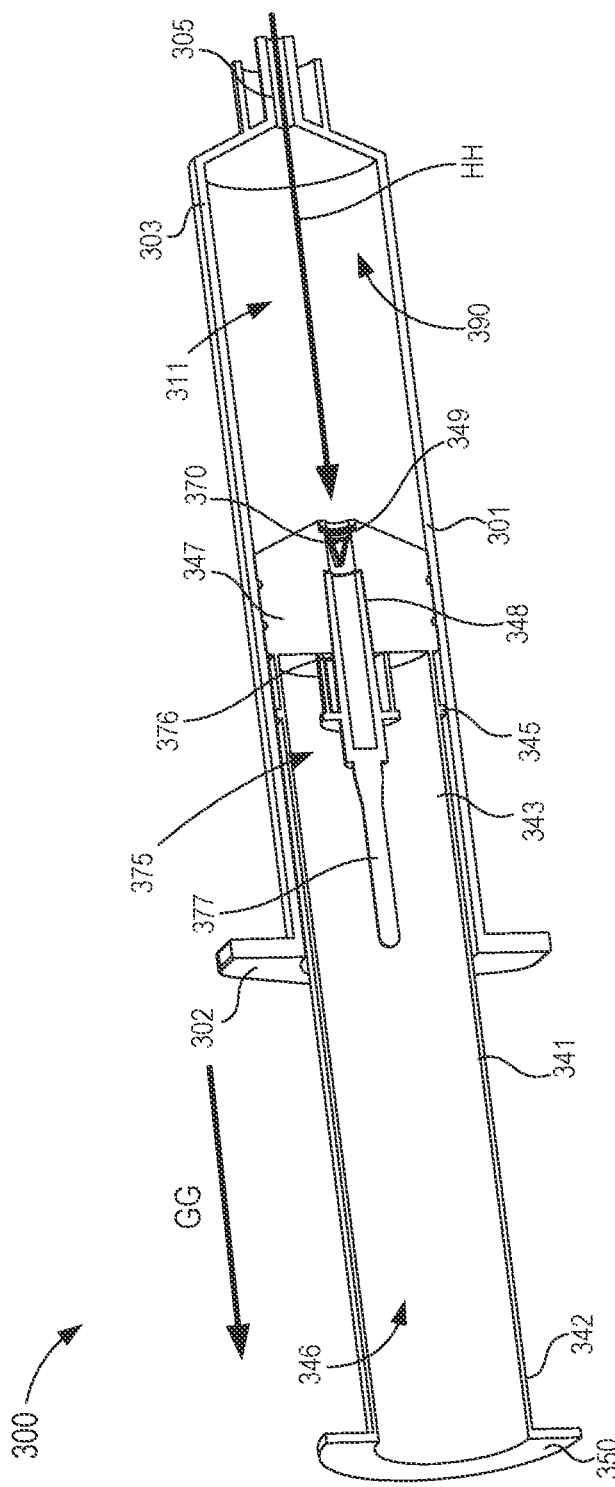
FIG. 10 is a cross-sectional view of the syringe-based transfer device of FIG. 7 taken along the line $X_2$-$X_2$, in a second configuration.

As shown by the arrow HH in FIG. 10, the port 305 and a portion of the inner volume 311 define a fluid flow path such that the second reservoir 390 is in fluid communication with the lumen-defining device. Therefore, the second reservoir 380 is placed in fluid communication with the portion of the patient (e.g., the vein, spinal cavity, etc.). Expanding further, the negative pressure within the second reservoir 390 produced by the movement of the plunger 347 introduces a suction force within the portion of the patient. Thus, a bodily-fluid is drawn through the port 305 and into the second reservoir 390. In addition, the bodily-fluid contained within the second reservoir 390 is substantially free from microbes generally found outside of the portion of the patient (e.g., dermally residing microbes, microbes within a lumen defined by the transfer device 300, microbes within the lumen defined by the lumen defining device, and/or any other undesirable microbe). Although not shown in FIGS. 7-10, in some embodiments, the syringe-based transfer device 300 can be coupled to a device in fluid communication with the patient that is also configured to reduce contamination of a patient sample. For example, in some embodiments, the syringe-based transfer device 300 can be used with a lumenless needle or the like such as those described in the '758 application.

While not shown in FIGS. 7-10, the actuator 341 can be moved from the third configuration to a fourth configuration to place the transfer device 300 in a fourth configuration. For example, in some embodiments, with the desired amount of bodily-fluid disposed within the second fluid reservoir 390, the transfer device 300 can be removed from the portion of the patient and disposed above or in a container (e.g., a vile, a test tube, a petri dish, a culture medium, a test apparatus, a cartridge or the like) such that a portion of the second amount of bodily-fluid can be tested. Expanding further, the user can apply a force to the engagement portion 350 to move the actuator 341 in the distal direction. Therefore, with the valve 370 in the closed configuration the force applied to the engagement portion 350 the actuator 341 in the distal direction relative to the housing 301 to expel a desired portion of the second amount of bodily-fluid from the lumen-defining device and into the container.

While the embodiments shown above describe an actuator being operative in directing a flow of a bodily-fluid, in some embodiments, a transfer device can include a flow control mechanism configured to direct a flow of the bodily-fluid. For example, FIGS. 11-15 illustrate a syringe-based transfer device 400 according to an embodiment. The syringe-based transfer device 400 (also referred to herein as "bodily-fluid transfer device," "fluid transfer device," or "transfer device") includes a housing 401, a flow control mechanism 430, and an actuator mechanism 440. Furthermore, the transfer device 400 is configured to include or define a first fluid reservoir 480 (also referred to herein as "first reservoir" or "pre-sample reservoir") and a second fluid reservoir 490 (also referred to herein as "second reservoir" or "sample reservoir"). The transfer device 400 can be any suitable shape, size, or configuration. For example, while shown in FIGS. 11 and 12 as being substantially cylindrical, the transfer device 400 can be square, rectangular, polygonal, and/or any other non-cylindrical shape. Moreover, portions of the transfer device 400 can be substantially similar to the corresponding portions of the transfer device 200, described above in reference to FIGS. 2-6. Therefore, such portions are not described in further detail herein and should be considered substantially similar unless explicitly described differently.

Figure 11:
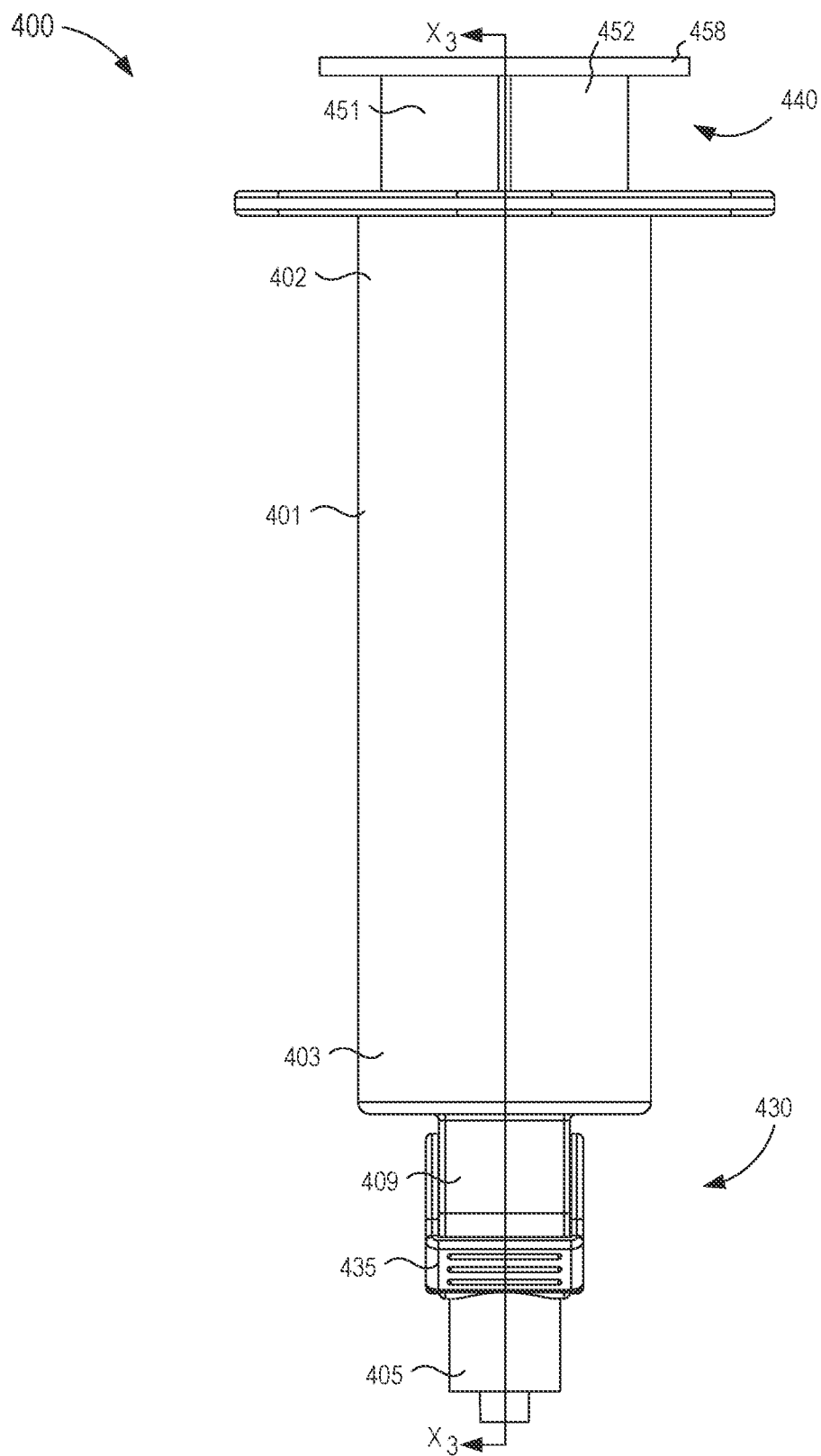
FIG. 11 is a front view of a syringe-based transfer device according to an embodiment, in a first configuration.
Figure 12:
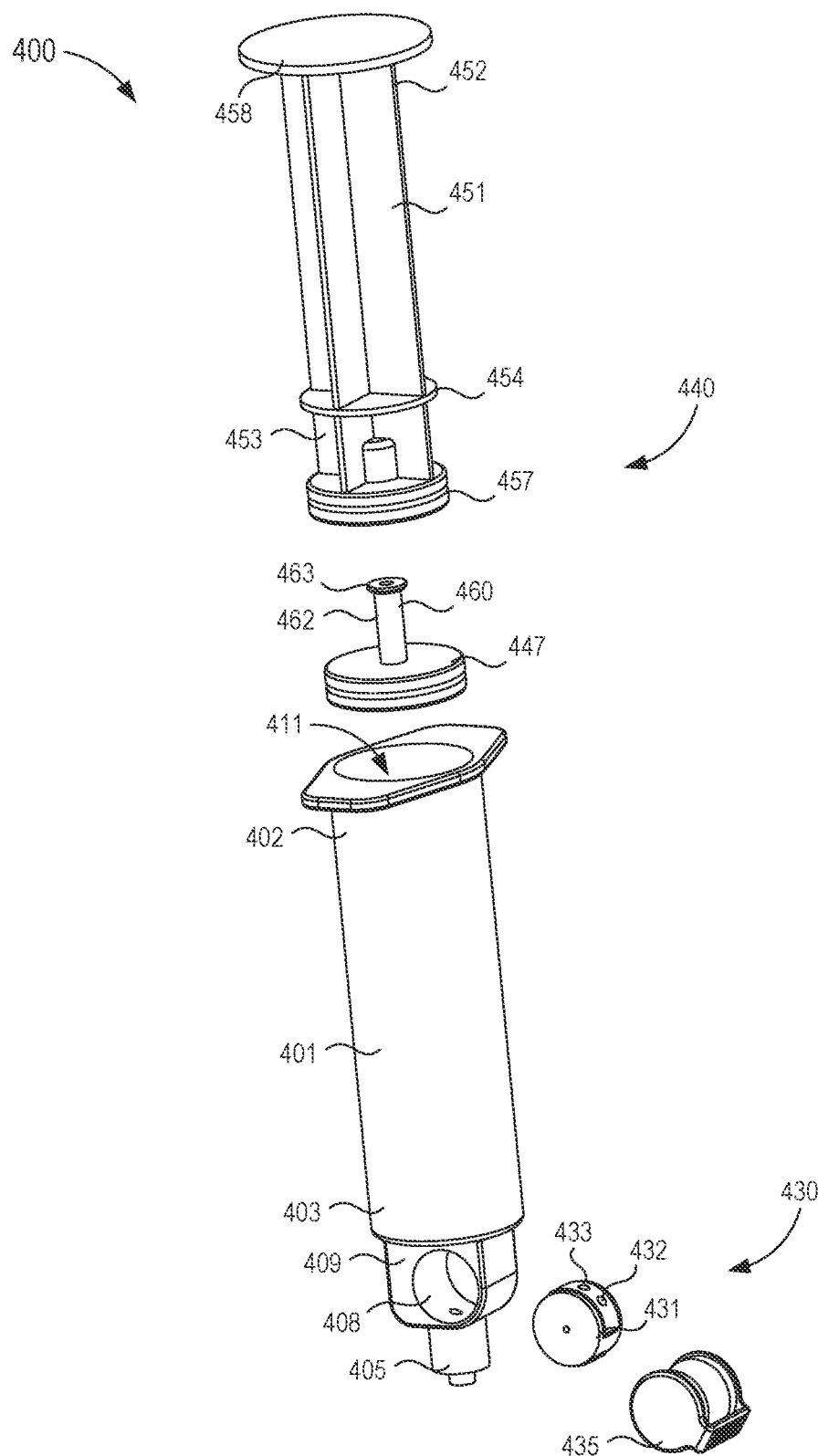
FIG. 12 is an exploded view of the syringe-based transfer device of FIG. 11.

As shown in FIGS. 11 and 12, the housing 401 includes a proximal end portion 402, a distal end portion 403, and defines an inner volume 411 therebetween. The proximal end portion 402 of the housing 401 is substantially open and is configured to receive at least a portion of the actuator mechanism 440 such that the portion of the actuator mechanism 440 is movably disposed within the inner volume 411. Furthermore, the inner volume 411 is configured to define, at least partially, the first fluid reservoir 480 the second fluid reservoir 490, as further described herein.

Figure 13:
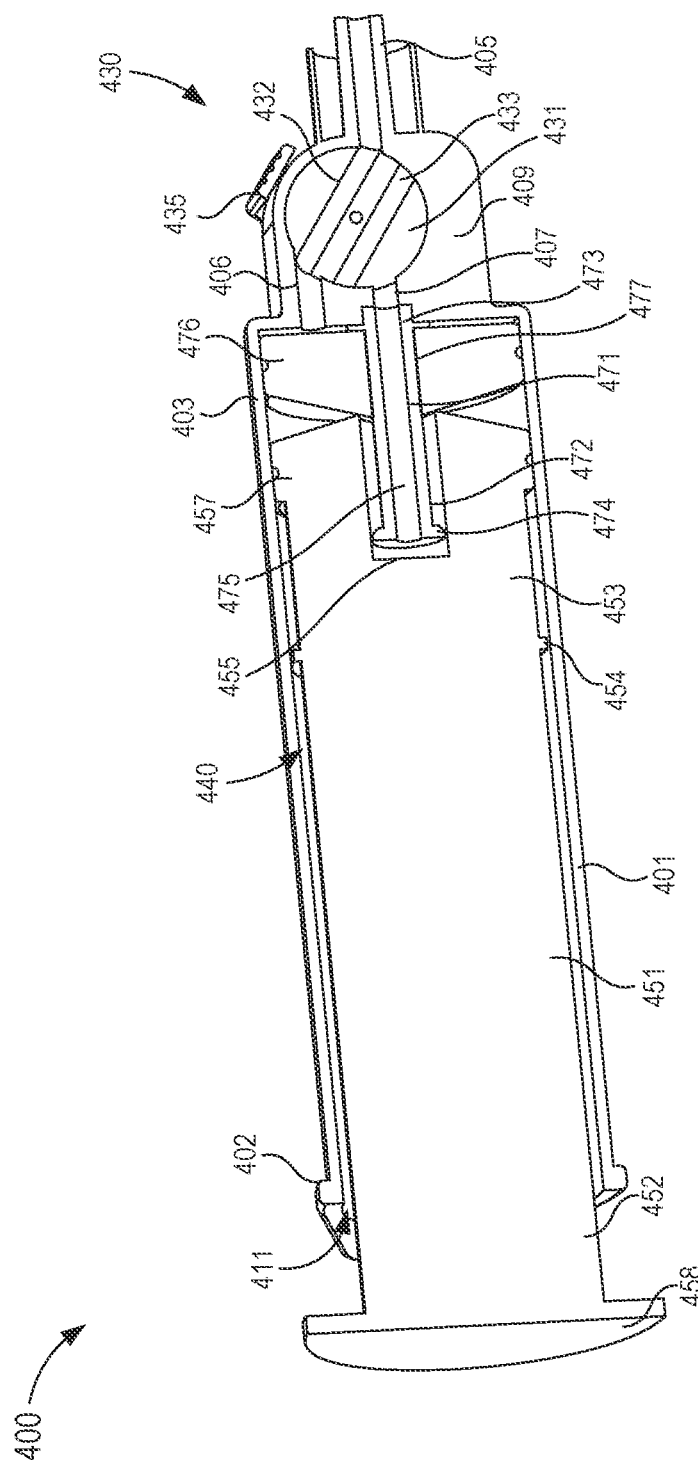
FIG. 13 is a cross-sectional view of the syringe-based transfer device of FIG. 11 taken along the line $X_3$-$X_3$, in the first configuration.

The distal end portion 403 of the housing 401 includes a port 405 and a diverter 409. The port 405 is configured to be coupled to or monolithically formed with a lumen-containing device, such as those described above. The diverter 409 defines a void 408 that movably receives a portion of the flow control mechanism 430. As shown in FIG. 13, the void 408 is in fluid communication with the port 405. The diverter 409 further defines a first lumen 406 in fluid communication with the void 408 and a first portion of the inner volume 411, and a second lumen 407 in fluid communication with the void 408 and a second portion of the inner volume 411. In this manner, the diverter 409 can selectively receive a flow of a bodily-fluid as further described herein.

Referring back to FIG. 12, the flow control mechanism 430 includes a first member 431 and a second member 435. As described above, at least a portion of the flow control mechanism 430 is movably disposed within a portion of the housing 401. More specifically the first member 431 is rotatably disposed within the void 408 of the diverter 409. The first member 431 defines a first lumen 432 and a second lumen 433 and defines a circular cross-sectional shape. In this manner, the first member 431 can be disposed within the void 408 such that a portion of the first member 431 forms a friction fit with the walls of the diverter 409 defining the void 408. For example, in some embodiments, the first member 431 is formed from silicone and has a diameter larger than the diameter of the void 408. In this manner, the diameter of the first member 431 is reduced when the first member 431 is disposed within the void 408. Thus, the outer surface of the first member 431 forms a friction fit with the inner surface of the walls defining the void 408. In other embodiments, the first member 431 can be any suitable elastomer configured to deform when disposed within the void 408 of the diverter 409.

The second member 435 is disposed substantially outside the void 408 and can be engaged by a user to rotate the flow control mechanism 430 between a first configuration and a second configuration. In addition, the first member 431 can be coupled to and/or otherwise engage the second member 445. For example, in some embodiments, the second member 435 can be coupled to the first member 431 via a mechanical fastener and/or adhesive. In other embodiments, the second member 435 and the first member 431 can be coupled in any suitable manner. Therefore, the first member 431 is configured to move concurrently with the second member 435 when the second member 435 is rotated relative to the housing 401. In this manner, the flow control mechanism 430 can be rotated to place the first lumen 432 or the second lumen 433 in fluid communication with the port 405, the first lumen 406, and/or the second lumen 407, as described in further detail herein.

As described above, the actuator mechanism 440 is disposed within the inner volume 411 and is movable between a first position (e.g., a distal position relative to the housing 401) and a second position (e.g., a proximal position relative to the housing 401). Furthermore, the movement of the actuator mechanism 440 relative to the housing 401 can move the transfer device 400 between a first, second, and third configuration, as further described herein. The actuator mechanism 440 includes a first member 470 and a second member 451. The first member 470 includes a shunt tube 471 and a plunger 476. The plunger 476 defines a channel 477 is configured to be movably disposed about the shunt tube 471. Similarly stated, the shunt tube 471 is disposed within the channel 477. The plunger 476 can be substantially similar in function to those described in detail above. For example, the plunger 476 can be configured to form a friction fit with a set of walls that define the inner volume 411 of the housing 401. In this manner, the plunger 476 and the walls defining the inner volume 411 form a substantially fluid tight seal. Similarly, the plunger 476 and the shunt tube 471 form a substantially fluid tight seal. Therefore, the plunger 476 fluidically isolates a portion of the inner volume 411 proximal of the plunger 476 from a portion of the inner volume 411 distal of the plunger 476.

The shunt tube 471 includes a proximal end portion 472 and a distal end portion 473. The distal end portion 473 is coupled to a portion of the diverter 409 such that a lumen 475 defined by the shunt tube 471 is in fluid communication with the second lumen 407 defined by the diverter 409. The proximal end portion 472 of the shunt tube 471 includes a protrusion 474 that is configured to engage the plunger 476 to substantially limit a proximal movement of the plunger 476 relative to the shunt tube 471, as further described herein.

The second member 451 of the actuator mechanism 440 includes a proximal end portion 452 and a distal end portion 453. The proximal end portion 452 includes an engagement portion 458 that can be engaged by a user (e.g., a phlebotomist, a nurse, a technician, a physician, etc.) to move at least a portion of the actuator mechanism 440 relative to the housing 401. The distal end portion 453 includes a plunger 457 configured to form a friction fit with the inner surface of the walls defining the inner volume 446 when the second member 451 is disposed with the inner volume 411. Similarly stated, the plunger 457 defines a fluidic seal with the inner surface of the walls defining the inner volume 411 such that a portion of the inner volume 411 proximal of the plunger 457 is fluidically isolated from a portion of the inner volume 411 distal of the plunger 457.

While not shown in FIGS. 11-15, the second member 451 can be at least temporarily coupled to the plunger 476 of the first member 470. For example, in some embodiments, the plunger 457 of the second member 451 can include a protrusion configured to be disposed within a groove defined by the plunger 476 of the first member 470. In this manner, the first member 470 and the second member 451 can be configured to collectively move, at least temporarily, within the housing 401, and can further be configured to move, at least temporarily, relative to each other.

As shown in FIG. 13, the distal end portion 453 defines a channel 459 configured to be selectively disposed about a portion of the shunt tube 471. Expanding further, the channel 459 can be configured to have a diameter that is sufficiently large such that the second member 451 can freely move about the shunt tube 471 (e.g., the shunt tube 471 and the walls defining the channel do not form a substantial friction fit.

In use, a user can engage the transfer device 400 to couple the port 405 to a proximal end portion of a lumen-defining device (not shown) such as, for example, a butterfly needle, a cannula assembly, a trocar (which in some cases is used to insert a catheter into a patient), or the like. With the port 405 physically coupled to the lumen-defining device, the port 405 is placed in fluid communication with the lumen defined by the lumen-defining device. Furthermore, the distal end portion of the lumen-defining device can be disposed within a portion of the body of a patient (e.g., a vein, spinal column, etc.). In this manner, the port 405 is placed in fluid communication with the portion of the body.

With the port 405 coupled to the lumen-defining device, a user (e.g., a phlebotomist, a nurse, a technician, a physician, or the like) can move the transfer device 400 from the first configuration to the second configuration. More specifically, the user can engage the engagement portion 458 of the second member 451 included in the actuator mechanism 440 to move the actuator mechanism 440 from its first configuration to its second configuration, thereby placing the transfer device 400 in the second configuration, as indicated by the arrow II in FIG. 14. In this manner, the actuator mechanism 440 is moved in a proximal direction relative to the housing 401

Figure 14:
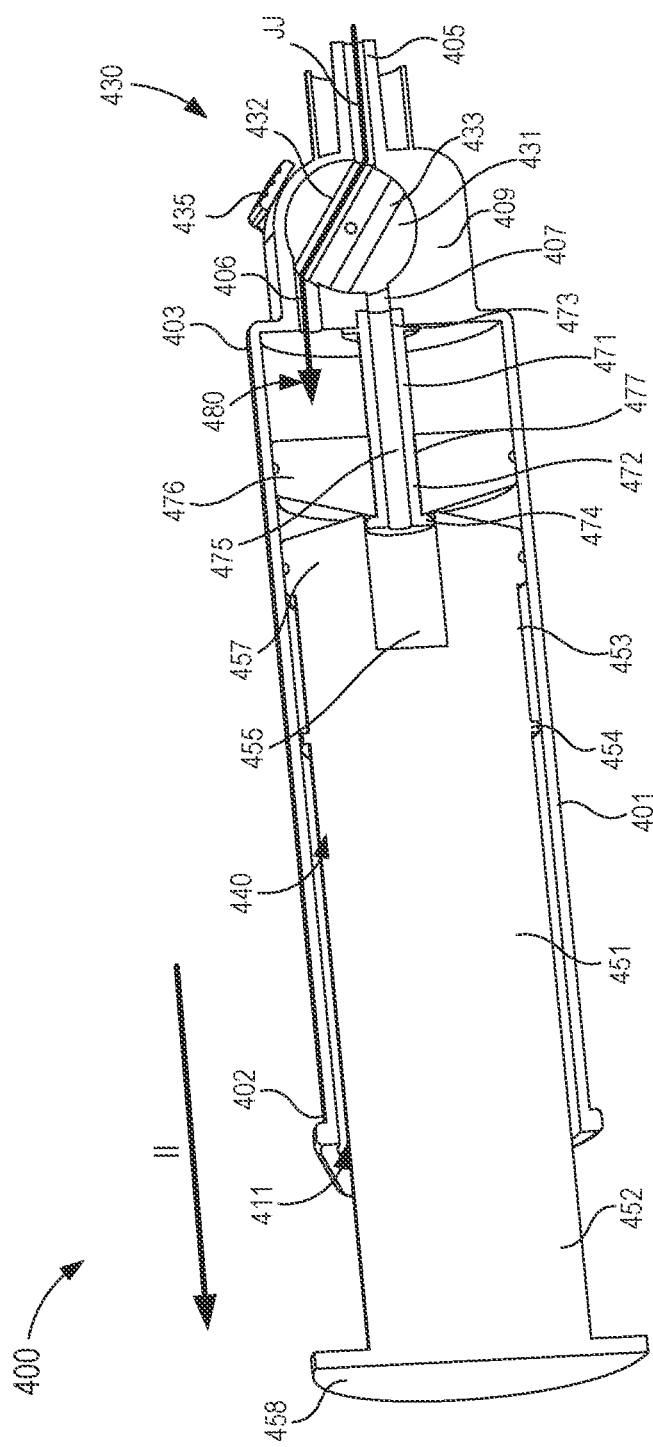
FIG. 14 is a cross-sectional view of the syringe-based transfer device of FIG. 11 taken along the line $X_3$-$X_3$, in a second configuration.

The arrangement of the actuator mechanism 440 is such that the proximal motion of the second member 451 moves the plunger 476 of the first member 470 in the proximal direction relative to the shunt tube 471. Expanding further, the first member 470 can be at least temporarily coupled to the second member 451 such that the first member 470 and the second member 451 move concurrently in the proximal direction relative to the housing 401. In this manner, the first member 470 moves in the proximal direction until the first member 470 is placed in contact with the protrusion 474 included in the shunt tube 471. Moreover, the proximal movement of the plunger 476 increases the volume of the portion of the inner volume 411 of the housing 401 that is distal of the plunger 476, thereby defining the first reservoir 480, as shown in FIG. 14. With the plunger 476 forming a fluid tight seal with the inner surface of the walls defining the inner volume 411 and with the shunt tube 471 about which the plunger 476 is disposed, the volume increase of the portion of the inner volume 411 can produce a negative pressure within the first reservoir 480.

While the transfer device 400 is placed in the second configuration, the flow control mechanism 430 can be maintained in the first configuration. In this manner, first member 431 of the flow control mechanism 430 can be disposed within the void 408 such that the first lumen 432 defined by the flow control mechanism 430 is in fluid communication with the port 405 and in fluid communication with the first lumen 406 defined by the diverter 409. In this manner, the port 405, the first lumen 432 defined by the flow control mechanism 430, and the first lumen 406 defined by the diverter 409 define a fluid flow path that places the first reservoir 480 in fluid communication with the lumen-defining device, as indicated by the arrow JJ in FIG. 14. Therefore, the first reservoir 480 is placed in fluid communication with the portion of the patient (e.g., the vein). Expanding further, the negative pressure within the first reservoir 480 produced by the movement of the plunger 476 (as indicated by the arrow II) introduces a suction force within the portion of the patient. Thus, a bodily-fluid is drawn through the port 405, the first lumen 432 defined by the flow control mechanism 430, and the first lumen 406 defined by the diverter 409 and into the fluid reservoir 480. In some embodiments, the bodily-fluid can contain undesirable microbes such as, for example, dermally-residing microbes and/or other external contaminants.

In some embodiments, the magnitude of the suction force can be modulated by moving the rotating the flow control mechanism 430 relative to the diverter 409. The rotation of the flow control mechanism 330 reduces the size of the fluid pathway (e.g., an inner diameter) between the port 405 and the first lumen 432 of the flow control mechanism 430 and the first lumen 406 of the diverter 409 and the first lumen 432 of the flow control mechanism 430, thereby reducing the suction force introduced into the vein of the patient.

With the desired amount of bodily-fluid transferred to the first reservoir 480, a user can engage the transfer device 400 to move the transfer device 400 from the second configuration to the third configuration. In some embodiments, the desired amount of bodily-fluid transferred to the first reservoir 480 is a predetermined amount of fluid (as described above). In some embodiments, the volume of the first reservoir 480 is sufficient to contain the first centiliter or few centiliters of bodily-fluid. In other embodiments, the first reservoir 480 can be configured to contain from about 0.1 ml to about 3.0 ml. In still other embodiments, the first reservoir 480 can be configured to contain from about 3.0 ml, 4.0 ml, 5.0 ml, 6.0 ml, 7.0 ml, 8.0 ml, 9.0 ml, 10.0 ml, 15.0 ml, 20.0 ml, 25.0 ml, 50 ml, or any volume or fraction of volume therebetween. In some embodiments, the predetermined amount of bodily-fluid (e.g., volume) is at least equal to the combined volume of the port 405, the first lumen 432 of the flow control mechanism 430, the first lumen 406 of the diverter 409, and the lumen-defining device. In other embodiments, the flow control mechanism 430 can be configured to automatically move from the first configuration to the second configuration to divert fluid flow without user intervention.

Figure 15:
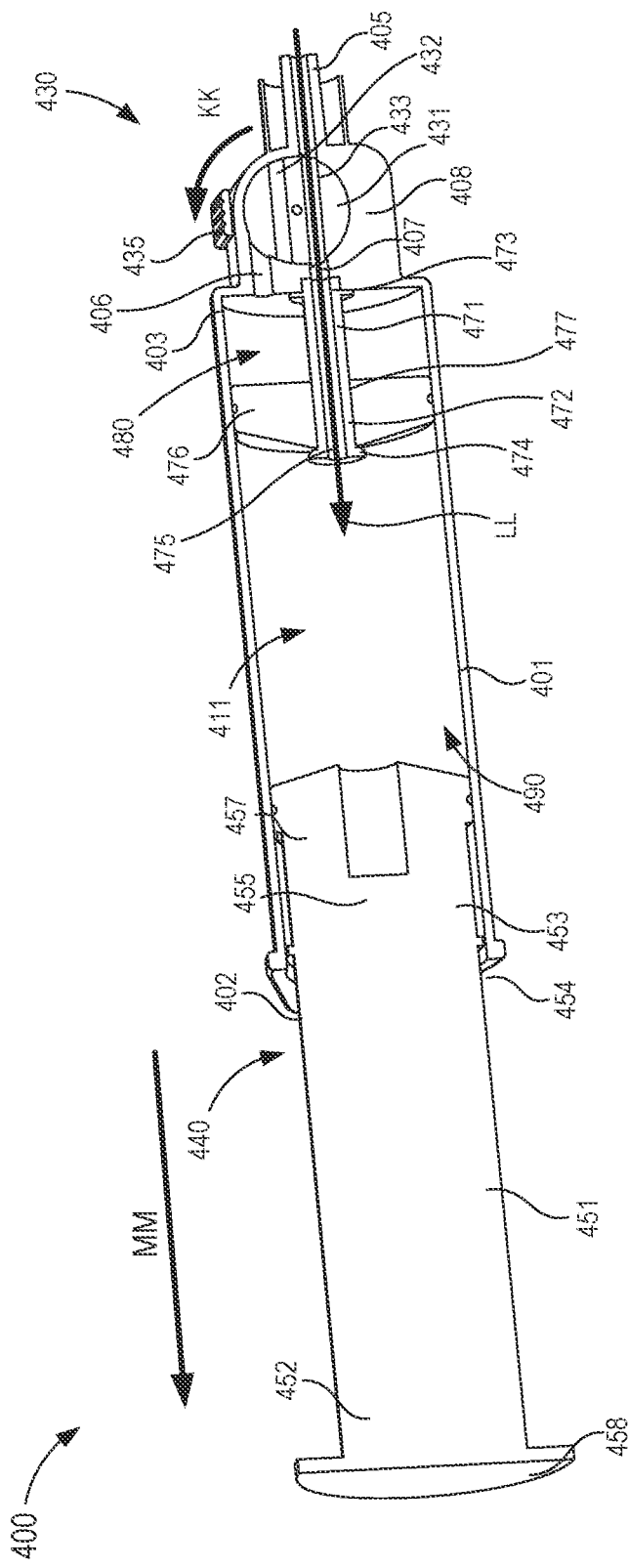
FIG. 15 is a cross-sectional view of the syringe-based transfer device of FIG. 11 taken along the line $X_3$-$X_3$, in a third configuration.

As shown in FIG. 15, the transfer device 400 can be moved from the second configuration to the third configuration by rotating the second member 435 of the flow control mechanism 430 relative to the diverter 409, as indicated by the arrow KK. In this manner, the flow control mechanism 430 is moved to the second configuration, and the first lumen 432 is fluidically isolated from the port 405 and the first lumen 406 of the diverter 409. Thus, the first reservoir 480 is fluidically isolated from a volume substantially outside the first reservoir 480. In addition, the second lumen 433 defined by the flow control mechanism 430 is placed in fluid communication with the port 405 and the second lumen 407 defined by the diverter 409. Therefore, the port 405, the second lumen 433 of the flow control mechanism 430, the second lumen 407 of the diverter 409, and the lumen 475 of the shunt tube 471 define a fluid flow path, as indicated by the arrow LL.

With the flow control mechanism 430 placed in the second configuration, the second member 451 of the actuator mechanism 440 can be moved from the second configuration to a third configuration. Expanding further, with the plunger 476 in contact with the protrusion 474 of the shunt 471, the second member 451 can be moved in the proximal direction to decouple the second member 451 from the plunger 476 (as described above the plunger 476 is at least temporarily coupled to the first member 451). In this manner, the second member 451 can be moved in the proximal direction relative to the first member 470, as indicated by the arrow MM in FIG. 15. The proximal movement of the second member 451 relative to the first member 470 increases the volume of the portion of the inner volume 411 that is proximal of the plunger 476 of the first member 470 and distal of the plunger 457 of the second member 451, thereby defining the second reservoir 490.

With the plunger 476 of the first member 470 and the plunger 457 of the second member 451 forming a fluid tight seal with the inner surface of the walls defining the inner volume 411, the volume increase of the portion of the inner volume 411 can produce a negative pressure within the first reservoir 490. Thus, the negative pressure within the second reservoir 490 is such that the negative pressure differential between the second reservoir 490 and the portion of the body of the patient introduces a suction force within the portion of the patient. Therefore, a desired amount of bodily-fluid is drawn through the port 405, the second lumen 433 of the flow control mechanism 430, the second lumen 407 of the flow diverter 409, and the lumen 475 defined by the shunt tube 471 and into the second reservoir 490. Moreover, the bodily-fluid disposed within the second reservoir 490 is fluidically isolated from the first, predetermined amount of bodily-fluid contained within the first reservoir 480.

Although not shown in FIGS. 11-15, in some embodiments, the syringe-based transfer device 400 can be coupled to a device in fluid communication with the patient that is also configured to reduce contamination of a patient sample. For example, in some embodiments, the syringe-based transfer device 400 can be used with a lumenless needle or the like such as those described in the '758 application.

While not shown in FIGS. 11-15, the actuator mechanism 440 can be moved from the third configuration to a fourth configuration to place the transfer device 400 in a fourth configuration. For example, in some embodiments, with the desired amount of bodily-fluid disposed within the second fluid reservoir 490, the transfer device 400 can be removed from the portion of the patient and disposed above or in a container (e.g., a vile, a test tube, a petri dish, a culture medium, a test apparatus, or the like) such that a portion of the second amount of bodily-fluid can be tested. Expanding further, the user can apply a force to the engagement portion 458 to move the second member 451 in the distal direction. Therefore, the force applied to the engagement portion 458 moves the second member 451 in the distal direction relative to the housing 301 to expel a desired portion of the second amount of bodily-fluid from the lumen-defining device and into the container.

Figure 16:
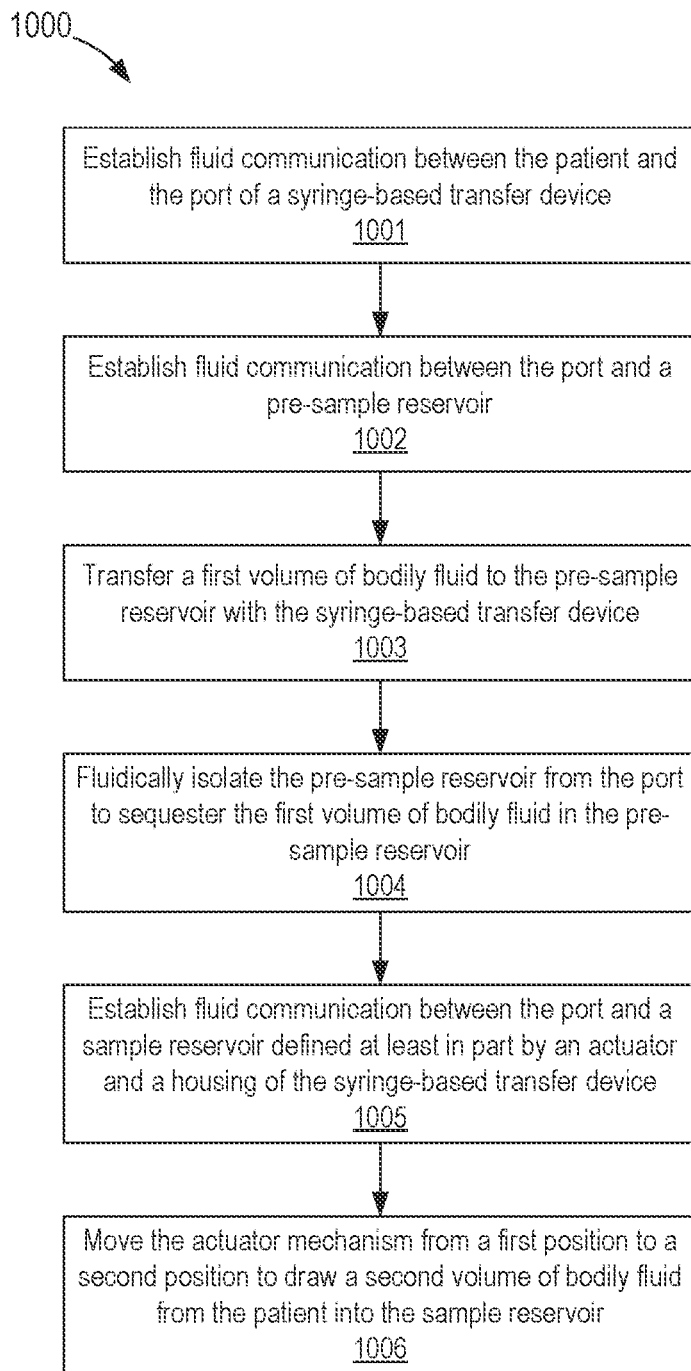
FIG. 16 is a flowchart illustrating a method of using a syringe-based transfer device to obtain a bodily fluid sample from a patient.

FIG. 16 is a flowchart illustrating a method 1000 of using a syringe-based transfer device to obtain a bodily fluid sample from a patient. The syringe-based transfer device can be any suitable device such as those described herein. Accordingly, the syringe-based transfer device can include a housing having a port configured to be coupled to the patient, and an actuator mechanism movably disposed in the housing. For example, the housing, the port, and the actuator mechanism can be substantially similar to or the same as the housing 201, the port 205, and the actuator mechanism 240, respectively, described above with reference to FIGS. 2-6.

The method 1000 includes establishing fluid communication between the patient and the port of the syringe-based transfer device, at 1001. For example, the port can be coupled to a proximal end portion of a lumen-defining device such as, for example, a butterfly needle, a cannula assembly, or the like that is in fluid communication with the patient (e.g., at least a distal end portion of the lumen-defining device is disposed in the body of the patient). With the port physically and fluidically coupled to the lumen-defining device, the port is placed in fluid communication with the body.

With the port coupled to the lumen-defining device, a user can establish fluid communication between the port and a pre-sample reservoir included in and/or defined by the syringe-based transfer device, at 1002. For example, the user can move the actuator mechanism from a first configuration to a second configuration, thereby placing the port in fluid communication with the pre-sample reservoir. In some embodiments, the movement of the actuator mechanism can increase an inner volume which, in turn, can produce a negative pressure within the pre-sample reservoir, as described above with reference to the transfer device 200 in FIG. 5. As described above, in some embodiments, the syringe-based transfer device can be manipulated to modulate the magnitude of suction force by controlling the movement of the actuator mechanism. In this manner, a first volume of bodily-fluid is transferred to the pre-sample reservoir with the syringe-based transfer device, at 1003. In some embodiments, the bodily-fluid can contain undesirable microbes such as, for example, dermally-residing microbes and/or other external contaminants.

The first volume of bodily-fluid can be any suitable volume. For example, in some embodiments, the first volume of bodily-fluid transferred to the pre-sample reservoir can be a predetermined volume. In some embodiments, the first volume can be, for example, about 0.1 ml, about 0.3 ml, about 0.5 ml, about 1.0 ml, about 2.0 ml, about 3.0 ml, about 4.0 ml, about 5.0 ml, about 10.0 ml, about 20 ml, about 50 ml, and/or any volume or fraction of a volume therebetween. In other embodiments, the first volume can be greater than 50 ml or less than 0.1 ml. In some embodiments, the first volume can substantially correspond to the size of the pre-sample reservoir 280. Once the first volume of bodily-fluid is transferred to the pre-sample, reservoir, the pre-sample reservoir is fluidically isolated from the port to sequester the first volume of bodily-fluid in the pre-sample reservoir, at 1004. For example, in some embodiments, the user can move the actuator mechanism and/or otherwise manipulate the syringe-based transfer device to fluidically isolate the pre-sample reservoir.

With the first amount fluidically isolated, fluid communication is established between the port and a sample reservoir defined at least in part by the actuator mechanism and the housing of the syringe-based transfer device, at 1005. For example, in some embodiments, the housing can define an inner volume in which the actuator mechanism is at least partially disposed. In some embodiments, the actuator mechanism can include a seal member or plunger that can form a substantially fluid tight seal with a set of walls defining the inner volume of the housing, thereby defining the sample reservoir. For example, the actuator mechanism and the housing can define the sample reservoir in a similar manner as described above with reference to the actuator mechanism 240, the housing 201, and the sample reservoir 290 of FIG. 6. As such, the actuator mechanism can be moved from a first position to a second position to draw a second volume of bodily-fluid from the patient into the sample reservoir, at 1006. With the first volume of bodily-fluid sequestered in the pre-sample reservoir, the second volume of bodily-fluid transferred to the sample reservoir can be substantially free from contaminants such as, for example, dermally residing microbes or the like.

While various embodiments have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain steps may be performed concurrently in a parallel process when possible, as well as performed sequentially as described above. Additionally, certain steps may be partially completed before proceeding to subsequent steps. For example, while the flow control mechanism 430 of the transfer device 400 is described above (with reference to FIG. 15) as being moved prior to the second member 451 of the actuator mechanism 440, in some embodiments, the second member 451 can be moved prior to or concurrently with the flow control mechanism 430.

While various embodiments have been particularly shown and described, various changes in form and details may be made. For example, while the flow control mechanism 430 is shown and described with respect to FIGS. 11-15 as being rotated in a single direction, in other embodiments, a flow control mechanism can be rotated in a first direction (e.g., in the direction of the arrow KK in FIG. 15) and a second direction, opposite the first. In such embodiments, the rotation in the second direction can be configured to move a transfer device through any number of configurations. In other embodiments, the rotation of the flow control mechanism in the second direction can be limited. For example, in some embodiments, the flow control mechanism can be limitedly rotated in the second direction to reduce the diameter of a flow path between the flow control mechanism and a lumen such as to reduce a suction force, as described above.

Although various embodiments have been described as having particular features and/or combinations of components, other embodiments are possible having any combination or sub-combination of any features and/or components from any of the embodiments described herein. For example, while the transfer device 400 is shown in FIGS. 11-15 as not including a valve (e.g., such as those described in the transfer devices 200 and 300), in some embodiments, the transfer device 400 can include a valve. For instance, the transfer device 400 can include a valve in the first lumen 406 of the diverter 409, or at any other suitable position.

The specific configurations of the various components can also be varied. For example, the size and specific shape of the various components can be different than the embodiments shown, while still providing the functions as described herein. More specifically, the size and shape of the various components can be specifically selected for a desired rate of bodily-fluid flow into a fluid reservoir.

The invention claimed is:

1. A blood transfer device for obtaining blood from a patient, comprising:
   a housing including a port for connecting to a needle that is inserted into the patient;
   a channel at least partially disposed in the housing, the channel defining at least a portion of a first fluid flow path for receiving a first volume of blood from the patient and contaminants that are present therein; and
   a valve and a valve seat disposed in the first fluid flow path,
   the valve configured to allow the first volume of blood to substantially fill the channel and to automatically close when pressure equalizes between an inlet and an outlet of the valve to prevent at least a portion of the first volume of blood from contaminating a second volume of blood received from the patient into a second fluid flow path of the blood transfer device.

2. The blood transfer device of claim 1, wherein the valve opens to allow at least a portion of the first volume of blood to flow past the valve.

3. The blood transfer device of claim 1, wherein the valve when closed is configured to allow creation of a negative pressure in the fluid flow path to draw the second volume of blood from the patient.

4. The blood transfer device of claim 1, wherein the valve when closed is in contact with the valve seat such that the valve forms a substantially fluid tight seal with walls defining the channel.

5. The blood transfer device of claim 1, wherein the valve is a one-way check valve.

6. The blood transfer device of claim 1, wherein the second fluid flow path is separate from the channel.

7. The blood transfer device of claim 1, further comprising a seal,
   the valve when open allows at least a portion of the first volume of blood to flow toward the seal.

8. A blood transfer device for obtaining blood from a patient, comprising:
   a housing;
   a channel at least partially disposed in the housing, the channel defining at least a portion of an inner volume for receiving a first volume of blood from the patient and contaminants that are present therein; and
   a valve disposed in the channel,
   the valve configured to open in response to a pressure difference between an inlet and an outlet of the valve,
   the valve configured to automatically close, after at least a portion of the first volume of blood is received in the inner volume, to enable negative pressure to develop within the housing so that a second volume of blood can be drawn into a fluid flow path of the blood transfer device that is separate from the inner volume, while preventing the portion of the first volume of blood from contaminating the second volume of blood.

9. The blood transfer device of claim 8, wherein the valve opens to allow at least a portion of the first volume of blood to flow past the valve.

10. The blood transfer device of claim 8, wherein the valve automatically closes in response to pressure equalizing between the inlet and the outlet of the valve.

11. The blood transfer device of claim 8, wherein the valve when closed is in contact with a valve seat disposed in the channel such that the valve forms a substantially fluid tight seal with walls defining the channel.

12. The blood transfer device of claim 8, wherein the valve is a one-way check valve.

13. The blood transfer device of claim 8, wherein:
   the housing includes a port for connecting to a needle that is inserted into the patient, and
   the channel receives the first volume of blood from the patient via the port.

14. The blood transfer device of claim 8, wherein:
   the housing includes a port for connecting to a sample container, and
   the blood transfer device, after receiving the second volume of blood from the patient, is configured to provide a sample of blood into the sample container.

15. The blood transfer device of claim 8, further comprising a seal,
the valve when open allows at least a portion of the first volume of blood to flow toward the seal.

16. A blood transfer device for obtaining blood from a patient, comprising:
a housing;
a channel at least partially disposed in the housing, the channel defining at least a portion of a first fluid flow path for receiving a first volume of blood from the patient and contaminants that are present therein; and
a valve disposed along the first fluid flow path,
the valve configured to open in response to a pressure difference between an inlet and an outlet of the valve and to close in response to pressure equalizing between the inlet and the outlet of the valve,
the blood transfer device in a first state configured to allow a first volume of blood to flow into the channel via the first fluid flow path,
the blood transfer device, after receiving the first volume of blood, configured to be in a second state in which the valve is closed,
the blood transfer device in the second state configured to receive a second volume of blood from the patient via a second fluid flow path, while preventing at least a portion of the first volume of blood from contaminating the second volume of blood.

17. The blood transfer device of claim 16, wherein the valve opens to allow at least a portion of the first volume of blood to flow past the valve.

18. The blood transfer device of claim 16, wherein the valve when closed is in contact with a valve seat such that the valve forms a substantially fluid tight seal with walls defining at least a portion of the first fluid flow path.

19. The blood transfer device of claim 16, wherein the second fluid flow path is separate from the channel.

20. The blood transfer device of claim 16, wherein:
the housing includes a port for connecting to a needle that is inserted into the patient, and
the second fluid flow path defined at least in part by the port.

21. The blood transfer device of claim 16, wherein:
the housing includes a port for connecting to a sample container, and
the blood transfer device, after receiving the second volume of blood from the patient, is configured to provide a sample of blood into the sample container.

22. The blood transfer device of claim 16, wherein the blood transfer device in the second state is configured to allow creation of a negative pressure in the second fluid flow path to draw the second volume of blood from the patient.

23. The blood transfer device of claim 16, further comprising a seal,
the valve when open allows at least a portion of the first volume of blood to flow toward the seal.

24. A blood transfer device for obtaining blood from a patient, comprising:
a housing including a port for connecting to a needle that is inserted into the patient;
a channel at least partially disposed in the housing; and
a one-way check valve in fluid communication with the channel, the one-way check valve configured to allow a first volume of blood to flow from the patient into the channel and to automatically close, after at least a portion of the first volume of blood has been received from the patient and when pressure equalizes between an inlet and an outlet of the valve, to prevent the portion of the first volume of blood and contaminants that are present therein from contaminating a second volume of blood received into the blood transfer device.

25. The blood transfer device of claim 24, wherein the one-way check valve when closed is in contact with a valve seat disposed in the channel such that the one-way check valve forms a substantially fluid tight seal with walls defining the channel.

26. The blood transfer device of claim 24, wherein the one-way check valve when closed enables negative pressure to develop within the housing so that the second volume of blood can be drawn into blood transfer device.

27. The blood transfer device of claim 24, wherein the port defines at least a portion of a fluid flow path for receiving the second volume of blood, the fluid flow path being separate from the channel.

28. The blood transfer device of claim 24, further comprising a seal,
the one-way check valve when open allows at least a portion of the first volume of blood to flow toward the seal.

29. A blood transfer device for obtaining blood from a patient, comprising:
a housing including a port for connecting to a needle that is inserted into the patient;
a channel at least partially disposed in the housing, the channel defining at least a portion of a first fluid flow path for receiving a first volume of blood from the patient and contaminants that are present therein; and
a valve and a valve seat disposed in the first fluid flow path,
the valve configured to allow the first volume of blood to substantially fill the channel and to automatically close to prevent at least a portion of the first volume of blood from contaminating a second volume of blood received from the patient into a second fluid flow path of the blood transfer device, and
the valve when closed configured to allow creation of a negative pressure in the fluid flow path to draw the second volume of blood from the patient.

30. The blood transfer device of claim 29, wherein the valve opens to allow at least a portion of the first volume of blood to flow past the valve.

31. The blood transfer device of claim 29, wherein the valve automatically closes in response to pressure equalizing between an inlet and an outlet of the valve.

32. The blood transfer device of claim 29, wherein the valve when closed is in contact with the valve seat such that the valve forms a substantially fluid tight seal with walls defining the channel.

33. The blood transfer device of claim 29, wherein the valve is a one-way check valve.

34. The blood transfer device of claim 29, wherein the second fluid flow path is separate from the channel.

35. The blood transfer device of claim 29, further comprising a seal,
the valve when open allows at least a portion of the first volume of blood to flow toward the seal.

36. A blood transfer device for obtaining blood from a patient, comprising:
a housing including a port for connecting to a needle that is inserted into the patient;
a channel at least partially disposed in the housing, the channel defining at least a portion of a first fluid flow path for receiving a first volume of blood from the patient and contaminants that are present therein; and a valve and a valve seat disposed in the first fluid flow path, the valve configured to allow the first volume of blood to substantially fill the channel and to automatically close to prevent at least a portion of the first volume of blood from contaminating a second volume of blood received from the patient into a second fluid flow path of the blood transfer device, the second fluid flow path separate from the channel.

37. The blood transfer device of claim 36, wherein the valve opens to allow at least a portion of the first volume of blood to flow past the valve.

38. The blood transfer device of claim 36, wherein the valve automatically closes in response to pressure equalizing between an inlet and an outlet of the valve.

39. The blood transfer device of claim 36, wherein the valve when closed is configured to allow creation of a negative pressure in the fluid flow path to draw the second volume of blood from the patient.

40. The blood transfer device of claim 36, wherein the valve when closed is in contact with the valve seat such that the valve forms a substantially fluid tight seal with walls defining the channel.

41. The blood transfer device of claim 36, wherein the valve is a one-way check valve.

42. The blood transfer device of claim 36, further comprising a seal,
the valve when open allows at least a portion of the first volume of blood to flow toward the seal.

43. A blood transfer device for obtaining blood from a patient, comprising:
a housing including a port for connecting to a needle that is inserted into the patient;
a channel at least partially disposed in the housing; and
a valve in fluid communication with the channel, the valve configured to allow a first volume of blood to flow from the patient into the channel and to automatically close, after at least a portion of the first volume of blood has been received from the patient, to prevent the portion of the first volume of blood and contaminants that are present therein from contaminating a second volume of blood received into the blood transfer device,
the valve when closed enabling a negative pressure to develop within the housing so that the second volume of blood can be drawn into blood transfer device.

44. The blood transfer device of claim 43, wherein the valve automatically closes in response to pressure equalizing between an inlet and an outlet of the valve.

45. The blood transfer device of claim 43, wherein the valve when closed is in contact with a valve seat disposed in the channel such that the valve forms a substantially fluid tight seal with walls defining the channel.

46. The blood transfer device of claim 43, wherein the port defines at least a portion of a fluid flow path for receiving the second volume of blood, the fluid flow path being separate from the channel.

47. The blood transfer device of claim 43, further comprising a seal,
the valve when open allows at least a portion of the first volume of blood to flow toward the seal.

48. The blood transfer device of claim 43, wherein the valve is a one-way check valve.

49. A blood transfer device for obtaining blood from a patient, comprising:
a housing including a port for connecting to a needle that is inserted into the patient;
a channel at least partially disposed in the housing; and
a valve in fluid communication with the channel, the valve configured to allow a first volume of blood to flow from the patient into the channel and to automatically close, after at least a portion of the first volume of blood has been received from the patient, to prevent the portion of the first volume of blood and contaminants that are present therein from contaminating a second volume of blood received into the blood transfer device,
wherein the port defines at least a portion of a fluid flow path for receiving the second volume of blood, the fluid flow path being separate from the channel.

50. The blood transfer device of claim 49, wherein the valve automatically closes in response to pressure equalizing between an inlet and an outlet of the valve.

51. The blood transfer device of claim 49, wherein the valve when closed is in contact with a valve seat disposed in the channel such that the valve forms a substantially fluid tight seal with walls defining the channel.

52. The blood transfer device of claim 49, wherein the valve when closed enables negative pressure to develop within the housing so that the second volume of blood can be drawn into blood transfer device.

53. The blood transfer device of claim 49, further comprising a seal,
the valve when open allows at least a portion of the first volume of blood to flow toward the seal.

54. The blood transfer device of claim 49, wherein the valve is a one-way check valve.

* * * * *